(12) United States Patent
Lewis et al.

(10) Patent No.: US 9,096,864 B2
(45) Date of Patent: Aug. 4, 2015

(54) TOBACCO INBRED PLANTS NCBEX1F, NCBEX1MS, AND NC EX90

(75) Inventors: Ramsey S. Lewis, Apex, NC (US); Ralph E. Dewey, Apex, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 13/407,421

(22) Filed: Feb. 28, 2012

(65) Prior Publication Data

US 2012/0216822 A1 Aug. 30, 2012

Related U.S. Application Data

(60) Provisional application No. 61/447,443, filed on Feb. 28, 2011, provisional application No. 61/546,573, filed on Oct. 13, 2011.

(51) Int. Cl.
| | | |
|---|---|---|
| *A01H 5/12* | (2006.01) | |
| *C12N 15/01* | (2006.01) | |
| *C12N 15/82* | (2006.01) | |
| *C12N 9/02* | (2006.01) | |
| *C12N 9/10* | (2006.01) | |

(52) U.S. Cl.
CPC .............. *C12N 15/8243* (2013.01); *A01H 5/12* (2013.01); *C12N 9/0077* (2013.01); *C12N 9/1007* (2013.01); *C12N 15/01* (2013.01)

(58) Field of Classification Search
None
See application file for complete search history.

(56) References Cited

U.S. PATENT DOCUMENTS

| | | | |
|---|---|---|---|
| 4,693,976 A | 9/1987 | Schilperoort et al. | |
| 4,732,856 A | 3/1988 | Federoff | |
| 4,762,785 A | 8/1988 | Comai | |
| 4,801,540 A | 1/1989 | Hiatt et al. | |
| 4,940,838 A | 7/1990 | Schilperoort et al. | |
| 4,945,050 A | 7/1990 | Sanford et al. | |
| 5,004,863 A | 4/1991 | Umbeck | |
| 5,013,658 A | 5/1991 | Dooner et al. | |
| 5,034,323 A | 7/1991 | Jorgensen et al. | |
| 5,104,310 A | 4/1992 | Saltin | |
| 5,107,065 A | 4/1992 | Shewmaker et al. | |
| 5,141,131 A | 8/1992 | Miller et al. | |
| 5,149,645 A | 9/1992 | Hoekema et al. | |
| 5,159,135 A | 10/1992 | Umbeck | |
| 5,177,010 A | 1/1993 | Goldman et al. | |
| 5,231,019 A | 7/1993 | Paszkowski et al. | |
| 5,302,523 A | 4/1994 | Coffee et al. | |
| 5,352,605 A | 10/1994 | Fraley et al. | |
| 5,378,619 A | 1/1995 | Rogers | |
| 5,384,253 A | 1/1995 | Krzyzek et al. | |
| 5,463,174 A | 10/1995 | Moloney et al. | |
| 5,464,763 A | 11/1995 | Schilperoort et al. | |
| 5,464,765 A | 11/1995 | Coffee et al. | |
| 5,469,976 A | 11/1995 | Burchell | |
| 5,472,869 A | 12/1995 | Krzyzek et al. | |
| 5,583,021 A | 12/1996 | Dougherty et al. | |
| 5,595,733 A | 1/1997 | Carswell et al. | |
| 5,614,399 A | 3/1997 | Quail et al. | |
| 5,641,664 A | 6/1997 | D'Halluin et al. | |
| 5,668,295 A | 9/1997 | Wahab et al. | |
| 5,679,558 A | 10/1997 | Gobel et al. | |
| 5,684,241 A | 11/1997 | Nakatani et al. | |
| 5,712,135 A | 1/1998 | D'Halluin et al. | |
| 5,713,376 A | 2/1998 | Berger | |
| 5,766,900 A | 6/1998 | Shillito et al. | |
| 5,929,304 A | 7/1999 | Radin et al. | |
| 6,002,070 A | 12/1999 | D'Halluin et al. | |
| 6,074,877 A | 6/2000 | D'Halluin et al. | |
| 6,907,887 B2 | 6/2005 | Conkling | |
| 6,953,040 B2 | 10/2005 | Atchley et al. | |
| 6,965,062 B2 * | 11/2005 | Rufty ..................... | 800/317.3 |
| 7,032,601 B2 | 4/2006 | Atchley et al. | |
| 7,700,834 B2 | 4/2010 | Xu et al. | |
| 7,700,851 B2 | 4/2010 | Xu | |
| 7,812,227 B2 | 10/2010 | Xu | |
| 7,855,318 B2 | 12/2010 | Xu | |
| 7,884,263 B2 | 2/2011 | Dewey et al. | |
| 8,058,504 B2 | 11/2011 | Xu | |
| 8,124,851 B2 * | 2/2012 | Dewey et al. .............. | 800/317.3 |
| 8,319,011 B2 | 11/2012 | Xu et al. | |
| 2002/0042934 A1 | 4/2002 | Staub et al. | |
| 2004/0103449 A1 | 5/2004 | Xu | |
| 2004/0111759 A1 | 6/2004 | Xu | |
| 2004/0117869 A1 | 6/2004 | Xu | |
| 2004/0162420 A1 | 8/2004 | Xu | |
| 2005/0132444 A1 | 6/2005 | Xu | |
| 2005/0160493 A9 | 7/2005 | Ratcliffe et al. | |

(Continued)

FOREIGN PATENT DOCUMENTS

| | | |
|---|---|---|
| EP | 0 120 516 A3 | 10/1984 |
| EP | 0 267 159 A3 | 5/1988 |

(Continued)

OTHER PUBLICATIONS

Julio, E. et al. Molecular Breeding (2008), vol. 21, pp. 369-381.*
Nikova, V. et al. Euphytica (1997), vol. 94, pp. 375-378.*
GenBank Accession No. DQ219344, dated Oct. 1, 2006, 2 pages.
GenBank Accession No. DQ219345, dated Oct. 1, 2006, 2 pages.
GenBank Accession No. DQ219346, dated Oct. 1, 2006, 2 pages.
GenBank Accession No. DQ219347, dated Oct. 1, 2006, 2 pages.
GenBank Accession No. DQ219348, dated Oct. 1, 2006, 2 pages.

(Continued)

*Primary Examiner* — Russell Kallis
(74) *Attorney, Agent, or Firm* — Myers, Bigel, Sibley & Sajovec, PA

(57) ABSTRACT

The present invention provides tobacco inbred plants NCBEX1F and NCBEX1MS, and NC EX90. The present invention also provides parts of such plants and products made from those parts. The present invention also includes progeny of the provided plants including hybrids.

28 Claims, 2 Drawing Sheets

(56) References Cited

U.S. PATENT DOCUMENTS

| | | |
|---|---|---|
| 2005/0178398 A1 | 8/2005 | Breslin et al. |
| 2005/0223442 A1 | 10/2005 | Xu |
| 2005/0244521 A1 | 11/2005 | Strickland et al. |
| 2006/0037096 A1 | 2/2006 | Xu |
| 2006/0037623 A1 | 2/2006 | Lawrence |
| 2006/0041949 A1 | 2/2006 | Xu |
| 2006/0157072 A1 | 7/2006 | Albino et al. |
| 2006/0185686 A1 | 8/2006 | Lawrence |
| 2006/0191548 A1 | 8/2006 | Strickland et al. |
| 2007/0149408 A1 | 6/2007 | Thomas et al. |
| 2007/0199097 A1* | 8/2007 | Xu et al. ............. 800/278 |
| 2007/0292871 A1 | 12/2007 | Xu |
| 2008/0076126 A1 | 3/2008 | Xu |
| 2008/0202541 A1 | 8/2008 | Dewey et al. |
| 2008/0245377 A1 | 10/2008 | Marshall et al. |
| 2009/0119788 A1 | 5/2009 | Mallmann et al. |
| 2009/0205072 A1 | 8/2009 | Dewey et al. |
| 2010/0218270 A1 | 8/2010 | Xu et al. |
| 2010/0235938 A1 | 9/2010 | Xu et al. |
| 2010/0235945 A1 | 9/2010 | Xu et al. |
| 2010/0235952 A1 | 9/2010 | Xu et al. |
| 2011/0048437 A1 | 3/2011 | Xu |
| 2011/0078817 A1 | 3/2011 | Xu |
| 2011/0174322 A1 | 7/2011 | Dewey et al. |
| 2011/0263328 A1 | 10/2011 | Yamashita et al. |
| 2012/0117933 A1 | 5/2012 | Dewey et al. |
| 2012/0118308 A1 | 5/2012 | Dewey et al. |
| 2012/0222689 A1 | 9/2012 | Xu et al. |

FOREIGN PATENT DOCUMENTS

| | | |
|---|---|---|
| EP | 0 292 435 B1 | 11/1988 |
| EP | 0 320 500 B1 | 6/1989 |
| EP | 0 116 718 B1 | 5/1990 |
| EP | 0 159 418 B1 | 5/1990 |
| EP | 0 176 112 B1 | 5/1990 |
| EP | 0 131 624 B1 | 9/1992 |
| EP | 0 627 752 B1 | 7/1997 |
| EP | 1 033 405 A3 | 9/2000 |
| EP | 0 290 799 B9 | 11/2003 |
| WO | WO 87/06614 A1 | 11/1987 |
| WO | WO 92/09696 A1 | 6/1992 |
| WO | WO 93/21335 A2 | 10/1993 |
| WO | WO 94/01930 A1 | 1/1994 |
| WO | WO 00/67558 A1 | 11/2000 |
| WO | WO 02/072758 A2 | 9/2002 |
| WO | WO 02/100199 A2 | 12/2002 |
| WO | WO 03/078577 A2 | 9/2003 |
| WO | WO 2004/035745 A2 | 4/2004 |
| WO | WO 2005/038018 A2 | 4/2005 |
| WO | WO 2005/038033 A2 | 4/2005 |
| WO | WO 2005/046363 A2 | 5/2005 |
| WO | WO 2005/111217 A2 | 11/2005 |
| WO | WO 2005/116199 A2 | 12/2005 |
| WO | WO 2006/022784 A1 | 3/2006 |
| WO | WO 2006/091194 A1 | 8/2006 |
| WO | WO 2006/120570 A2 | 11/2006 |
| WO | WO 2008/070274 A2 | 6/2008 |
| WO | WO 2008/076802 A2 | 6/2008 |
| WO | WO 2009/064771 A2 | 5/2009 |
| WO | WO 2011/088180 A1 | 7/2011 |
| WO | WO 2012/118779 A1 | 9/2012 |

OTHER PUBLICATIONS

GenBank Accession No. DQ219349, dated Oct. 1, 2006, 2 pages.
GenBank Accession No. DQ219350, dated Oct. 1, 2006, 2 pages.
GenBank Accession No. DQ219351, dated Oct. 1, 2006, 2 pages.
GenBank Accession No. DQ219352, dated Oct. 1, 2006, 2 pages.
GenBank Accession No. DQ350312, dated Dec. 31, 2006, 2 pages.
GenBank Accession No. DQ350313, dated Dec. 31, 2006, 2 pages.
GenBank Accession No. DQ350314, dated Dec. 31, 2006, 2 pages.
GenBank Accession No. DQ350315, dated Dec. 31, 2006, 2 pages.
GenBank Accession No. DQ350316, dated Dec. 31, 2006, 2 pages.
GenBank Accession No. DQ350317, dated Dec. 31, 2006, 2 pages.
GenBank Accession No. DQ350318, dated Dec. 31, 2006, 2 pages.
GenBank Accession No. DQ350319, dated Dec. 31, 2006, 2 pages.
GenBank Accession No. DQ350320, dated Dec. 31, 2006, 2 pages.
GenBank Accession No. DQ350321, dated Dec. 31, 2006, 2 pages.
GenBank Accession No. DQ350322, dated Dec. 31, 2006, 2 pages.
GenBank Accession No. DQ350323, dated Dec. 31, 2006, 2 pages.
GenBank Accession No. DQ350324, dated Dec. 31, 2006, 2 pages.
GenBank Accession No. DQ350325, dated Dec. 31, 2006, 2 pages.
GenBank Accession No. DQ350326, dated Dec. 31, 2006, 2 pages.
GenBank Accession No. DQ350327, dated Dec. 31, 2006, 2 pages.
GenBank Accession No. DQ350328, dated Dec. 31, 2006, 2 pages.
GenBank Accession No. DQ350329, dated Dec. 31, 2006, 2 pages.
GenBank Accession No. DQ350330, dated Dec. 31, 2006, 2 pages.
GenBank Accession No. DQ350331, dated Dec. 31, 2006, 2 pages.
GenBank Accession No. DQ350332, dated Dec. 31, 2006, 2 pages.
GenBank Accession No. DQ350333, dated Dec. 31, 2006, 2 pages.
GenBank Accession No. DQ350334, dated Dec. 31, 2006, 2 pages.
GenBank Accession No. DQ350335, dated Dec. 31, 2006, 2 pages.
GenBank Accession No. DQ350336, dated Dec. 31, 2006, 2 pages.
GenBank Accession No. DQ350337, dated Dec. 31, 2006, 2 pages.
GenBank Accession No. DQ350338, dated Dec. 31, 2006, 2 pages.
GenBank Accession No. DQ350339, dated Dec. 31, 2006, 2 pages.
GenBank Accession No. DQ350340, dated Dec. 31, 2006, 2 pages.
GenBank Accession No. DQ350341, dated Dec. 31, 2006, 2 pages.
GenBank Accession No. DQ350342, dated Dec. 31, 2006, 2 pages.
GenBank Accession No. DQ350343, dated Dec. 31, 2006, 2 pages.
GenBank Accession No. DQ350344, dated Dec. 31, 2006, 2 pages.
GenBank Accession No. DQ350345, dated Dec. 31, 2006, 2 pages.
GenBank Accession No. DQ350346, dated Dec. 31, 2006, 2 pages.
GenBank Accession No. DQ350347, dated Dec. 31, 2006, 2 pages.
GenBank Accession No. DQ350348, dated Dec. 31, 2006, 2 pages.
GenBank Accession No. DQ350349, dated Dec. 31, 2006, 2 pages.
GenBank Accession No. DQ350350, dated Dec. 31, 2006, 2 pages.
GenBank Accession No. DQ350351, dated Dec. 31, 2006, 2 pages.
GenBank Accession No. DQ350352, dated Dec. 31, 2006, 2 pages.
GenBank Accession No. DQ350353, dated Dec. 31, 2006, 2 pages.
GenBank Accession No. DQ350354, dated Dec. 31, 2006, 2 pages.
GenBank Accession No. DQ350355, dated Dec. 31, 2006, 2 pages.
GenBank Accession No. DQ350356, dated Dec. 31, 2006, 2 pages.
GenBank Accession No. DQ350357, dated Dec. 31, 2006, 2 pages.
GenBank Accession No. DQ350358, dated Dec. 31, 2006, 2 pages.
GenBank Accession No. DQ350359, dated Dec. 31, 2006, 2 pages.
GenBank Accession No. DQ350360, dated Dec. 31, 2006, 2 pages.
GenBank Accession No. DQ350361, dated Dec. 31, 2006, 2 pages.
GenBank Accession No. DQ350362, dated Dec. 31, 2006, 2 pages.
GenBank Accession No. DQ350363, dated Dec. 31, 2006, 2 pages.
GenBank Accession No. DQ205656, dated Jan. 18, 2007, 2 pages.
GenBank Accession No. ABA07806, dated Mar. 7, 2007, 2 pages.
GenBank Accession No. DQ131887, dated Mar. 7, 2007, 2 pages.
Ghosh, "Polyamines and plant alkaloids," *Indian J. Exp. Biol.*, 38:1086-1091 (2000).
Goldrick et al., "Molecular Genetic Analysis of the User Group Associated with Two Mouse Light Chain Genetic Markers," *J Exp Med* 162:713-728 (1985).
Graham-Lorence et al., "P450s: Structural similarities and functional differences," *FASEB J.* 10:206-214 (1996).
Guo et al., "Protein Tolerance to Random Amino Acid Change," *PNAS*, 101(25):9205-9210 (2004).
Hao et al., "Mechanism of Nicotine N-Demethylation in Tobacco Cell Suspension Cultures," *Phytochemistry*, 41(2):477-482 (1995).
Hao et al., "Nicotine N-Demethylase in Cell-Free Preparations from Tobacco Cell Cultures," *Phytochemistry*, 42(2):325-329 (1996).
Hao et al., "Evidence in Favour of an Oxidative N-Demethylation of Nicotine to Nornicotine in Tobacco Cell Cultures," *Journal Plant Physiology*, 152:420-426 (1998).
Haseloff et al., "Simple RNA enzymes with new and highly specific endoribonuclease activities," *Nature*, 334:585-591 (1998).
Hayes et al., "Blotting techniques for the study of DNA, RNA, and proteins," *BMJ*, 299(14):965-968 (1989).
Hecht et al., "The relevance of tobacco-specific nitrosamines to human cancer," *Cancer Surveys*, 8(2):273-294 (1989).

(56) References Cited

OTHER PUBLICATIONS

Hecht, "Biochemistry, Biology, and Carcinogenicity of Tobacco-Specific N-Nitrosamines," *Chemical Research in Toxicology*, 11(6):559-603 (1998).

Helene et al., "Control of Gene Expression by Triple Helix-Forming Oligonucleotides,"*Ann. N.Y. Acad. Sci.*, 660:27-36 (1992).

Helene, "The anti-gene strategy: control of gene expression by triplex-fanning-oligonucleotides," *Anti-Cancer Drug Des.*, 6:569-584 (1991).

Helliwell et al., "High-throughput vectors for efficient gene silencing in plants," *Funct. Plant Biol.*, 29:1217-1225 (2002).

Henikoff et al., "Single-Nucleotide Mutations for Plant Functional Genomics," *Annu. Rev. Plant Biol.*, 54:375-401 (2003).

Herbik et al., "Isolation, characterization and cDNA cloning of nicotianamine synthase from barley," *Eur J Biochem*, 265(1): 231-9 (1999).

Hibino et al., "Increase of Cinnamaldehyde Groups in Lignin of Transgenic Tobacco Plants Carrying an Antisense Gene for Cinnamyl Alcohol Dehydrogenase," *Biosci. Biotec. Biochem*, 59:929-931 (1995).

Hildering et al., "Chimeric Structure of the Tomato Plant After Seed Treatment with EMS and X-Rays," The Use of Induced Mutations in Plant Breeding, Pergamon Press, pp. 317-320 (1965).

Hill et al., "Functional analysis of conserved histidines in ADP-glucose pyrophosphorylase from *Escerichia coli*," *Biochem. Biophys. Res. Commun.*, 244:573-577 (1998) (Abstract only).

Hoekema et al., "A binary plant vector strategy based on separation of the vir- and T-region of the *Agrobacterium tumefaciens* Ti-plasmid," *Nature*, 303:179-180 (1983).

Hoffmann et al., "Tobacco-specific N-nitrosamines and Areca-derived N-nitrosamines: chemistry, biochemistry, carcinogenicity, and relevance to humans," *Journal of Toxicology and Environmental Health*, 41:1-52(1994).

Huang et al., "Insights into Regulation and Function of the Major Stress-hlduced hsp70 Molecular Chaperone In Vivo: Analysis of Mice with Targeted Gene Disruption of the *hsp70. 1* or *hsp70.3* Gene," *Mol Cell Biol*, 21(24):8575-8591 (2001).

Ingelbrecht et al., "Posttranscriptional silencing of reporter transgenes in tobacco correlates with DNA methylation," *PNAS*, 91:10502-10506 (1994).

International Preliminary Report on Patentability in PCT/US07/087386 mailed Jun. 25, 2009, 6 pages.

International Search Report and the Written Opinion of the International Searching Authority, or the Declaration mailed on May 4, 2012, in International Application No. PCT/US2012/026864 (13 pages).

International Search Report and the Written Opinion of the International Searching Authority, or the Declaration mailed on Jul. 4, 2012, in International Application No. PCT/US2012/026795 (15 pages).

Isshiki et al., "Nonsense-mediated decay of mutant waxy mRNA in rice," *Plant Physiology*, 125:1388-1395 (2001).

Jack et. al., "Relative stability of nicotine to nornicotine conversion in three burley cultivars," Coresta Congress, Kyoto, Agro-Phyto groups, Abstract AP2 (2004).

Johnston et al., "Dosage-sensitive function of retinoblastoma related and convergent epigenetic control are required during the *Arabidopsis* life cycle," *PLoS Genet*, 6(6):e1000988 (2010).

Jorgensen et al., "Chalcone synthase cosuppression phenotypes in petunia flowers: comparison of sense vs. antisense constructs and single-copy vs. complex T-DNA sequences," *Plant Mol. Biol.*, 31:957-973 (1996).

Julio et al. "Reducing the content of nomicotine in tobacco via targeted mutation breeding," *Mol. Breeding*, 21:369-381 (2008).

Julio et al., Targeted Mutation Breeding as a tool for tobacco crop improvement, presentation made in Oct. 2008.

Kafri et al., "The regulatory utilization of genetic redundancy through responsive backup circuits," *PNAS*, 103(31):11653-11658 (2006).

Kempin et al., "Targeted disruption in *Arabidopsis*," *Nature*, 389:802-803 (1997).

Keskin et al., "A new, structurally nonredundant, diverse data set of protein-protein interfaces and its implications," *Protein Science*, 13:1043-1055 (2004).

Kim et al., "*Arabidopsis* CYP85A2, a Cytochrome P450, Mediates the Baeyer-Villiger Oxidation of Castasterone to Brassinolide in Brassinosteroid Biosynthesis," *Plant Cell*, 17:2397-2412 (2005).

Klahre et al., "High molecular weight RNAs and small interfering RNAs induce systemic posttranscriptional gene silencing in plants," *PNAS*, 99:11981-11986 (2002).

Klink et al., The Efficacy of RNAi in the Study of the Plant Cytoskeleton, *J Plant Growth Regul.*, 19:371-384 (2000).

Koornneff, "Chapter 1: Classical mutagenesis in higher plants," *Molecular Plant Biology*, Gilmartin and Bowler, ed., Oxford University Press, pp. 1-11 (2002).

Koshinsky et al., "Cre-lox site-specific recombination between *Arabidopsis* and tobacco chromosomes," *Plant J*. 23(6):715-722 (2000).

Kusaba et al., "*Low glutelin contentl*: A Dominant Mutation That Suppresses the *Glutelin* Multigene Family via RNA Silencing in Rice," *Plant Cell*, 15:1455-1467 (2003).

Kynast et al., "Dissecting the maize genome by using chromosome addition and radiation hybrid lines," *PNAS*, 101(26):9921-9926 (2004).

Lazaret al., "Transforming Growth Factor α Mutation of Aspartic Acid 47 and Leucine 48 Results in Different Biological Activities," *Mol. Cell. Biol.*, 8(3):1247-1252 (1988).

Levin et al., "Methods of double-stranded RNA-mediated gene inactivation in *Arabidopsis* and their use to define an essential gene in methionine biosynthesis," *Plant Mol. Biol.*, 44:759-775 (2000).

Lewis et al., Three nicotine demethylase genes mediate nornicotine biosynthesis in *Nicotiana tabactum* L.: Functional characterization of the CYP82E10 gene, *Phytochemistry*, 71:1988-1998 (2010).

Lewis, et al. "RNA interference (RNAi)-induced suppression of nicotine demethylase activity reduces levels of a key carcinogen in cured tobacco leaves." *Plant Biotechnology Journal*, 6:1-9 (2008).

Liu et al., "High-Stearic and High-Oleic Cottonseed Oils Produced by Hairpin RNA-Mediated Post-Transcriptional Gene Silencing," *Plant Physiol.*, 129:1732-1743 (2002).

Liu et al., "Identification and characterization of HTD2: a novel gene negatively regulating tiller bud outgrowth in rice," *Planta*, 230(4):649-658 (2009).

Liu et al. "Genetic and transformation studies reveal negative regulation of ERS 1 ethylene receptor signaling in *Arabidopsis*," *BMC Plant Biol*, 10:60-73 (2010).

Maher, "DNA Triple-Helix Formation: An Approach to Artificial Gene Repressors?" *BioEssays*, 14(12):807-815 (1992).

Maniatis et al., "Regulation of inducible and tissue-specific gene expression,"*Science*, 236:1237-1245 (1987).

Mansoor et al. "Engineering novel traits in plants through RNA interference," *Trends in Plant Science*, 11(11):1-7 (2006).

Maquat, "Nonsense-mediated mRNA decay," *Curr. Biol.*, 12(6):R196-R197 (2002).

Matthew, "RNAi for plant functional genomics," *Comparative and Functional Genomics*, 5:240-244 (2004).

McDougall et al., "Detection of Viral DNA and RNA by In Situ Hybridization,"*J. Histochem. Cytochem.*, 34:33-38 (1986).

McKinney et al., "Sequence-based identification of T-DNA insertion mutations in *Arabidopsis*: actin mutants act2-1 and act4-1,"*Plant J.*, 8(4):613-622 (1995).

Mesnard et al., "Evidence for the involvement of tetrahydrofolate in the demethylation of nicotine by *Nicotiana plumbaginifolia* cell-suspension cultures," *Planta*, 214:911-919 (2002).

Mette et al., "Transcriptional silencing and promoter methylation triggered by double-stranded RNA," *EMBO J*. 19(19):5194-5201 (2000).

Mol et al., "Regulation of plant gene expression by antisense RNA," *FEBS Lett.*, 268(2):427-430 (1990).

Napoli et al., "Introduction of a Chimeric Chalcone Synthase Gene into Petunia Results in Reversible Co-Suppression of Homologous Genes in trans," *Plant Cell*, 2:279-289 (1990).

(56) References Cited

OTHER PUBLICATIONS

Nawrath et al., "Salicylic Acid Induction-Deficient Mutants of *Arabidopsis* Express *PR-2* and *PR-5* and Accumulate High Levels of Camalexin after Pathogen Inoculation," *Plant Cell*, 11:1393-1404 (1999).
Needleman et al., "A General Method Applicable to the Search for Similarities in the Amino Acid Sequence of Two Proteins," *J. Mol. Biol*, 48:443-453 (1970).
Nelson et al., "Comparative Genomics of Rice and *Arabidopsis*, Analysis of 727 Cytochrome P450 Genes and Pseudogenes from a Monocot and a Dicot," *Plant Physiol.*, 135:756-772 (2004).
Nelson et al., "Comparison of cytochrome P450 (*CYP*) genes from the mouse and human genomes, including nomenclature recommendations for genes, pseudogenes and alternative-splice variants," *Phannacogenetics*, 14:1-18 (2004).
Ng et al., "Specific Detection and Confirmation of *Campylobacter jejuni* by DNA Hybridization and PCR," *Appl. Environ. Microbiol.* 63(11):4558-4563 (1997).
Nishihara et al., "Flavanoid components and flower color change in transgenic tobacco plants by suppression of chalcone isomerase gene," *FEBS Lett.*, 579:6074-6078 (2005).
Odell et al., "Identification of DNA sequences required for activity of the cauliflower mosaic virus 35S promoter," *Nature*, 313:810-812 (1985).
Office Action mailed on Oct. 18, 2006, in U.S. Appl. No. 10/293,252.
Office Action mailed on Oct. 30, 2006, in U.S. Appl. No. 10/686,947.
Office Action mailed on Nov. 14, 2006, in U.S. Appl. No. 10/387,346.
Office Action mailed on Nov. 14, 2006, in U.S. Appl. No. 10/340,861.
Office Action mailed on May 4, 2007, in U.S. Appl. No. 10/943,507.
Office Action mailed on Jun. 12,2007, in U.S. Appl. No. 10/934,944.
Ogita et al., "Application of RNAi to confirm theobromine as the major intermediate for caffeine biosynthesis in coffee plants with potential for construction of decaffeinated varieties," *Plant Mol. Biol.*, 54:931-941 (2004).
Ohshima et al "Nucleotide sequence of the *PR-1* gene of *Nicotiana tabacum*," *FEBS Letters*, 225:243-246 (1987).
Oliver et al., "Inhibition of tobacco NADH-hydroxypyruvate reductase by expression of a heterologous antisense RNA derived from a cucumber cDNA: Implications for the mechanism of action of antisense RNAs,"*Mol. Gen Genet*, 239(3):425-34 (1993).
Pearson et al., "Improved tools for biological sequence comparison," *PNAS*, 85:2444-2448 (1988).
Peele et al., "Formation of Tobacco-specific Nitrosamines in Flue-cured Tobacco," CORESTA Meeting, Agro-Phyto Groups, Suzhou, China (1999).
Pickett et al., "Seeing Double: Appreciating Genetic Redundancy," *Plant Cell*, 7:1347-1356 (1995).
Plant Variety Protection Office (USDA-AMS, Beltsville, MD, http://www.ars-grin.gov/cgi-bin/npgs/htmllpvp.pl?Tobbaco, accessed Feb. 2009).
Puchta et al., "Two different but related mechanisms are used in plants for the repair of genomic double-strand breaks by homologous recombination," *PNAS*, 93:5055-5060 (1996).
Qin et al., "Cre recombinase-mediated site-specific recombination between plant chromosomes," *PNAS*, 91:1706-1710 (1994).
Qiu et al. "A computational study of off-target effects of RNA interference." *Nucleic Acids Research*, 33(6)1834-1847 (2005).
Ralston et al., "Cloning, Heterologous Aristolochene-1,3-Dihydroxylase from Expression, and Functional Characterization of 5-epi-Tobacco (*Nicotiana tabacum*)," *Arch. Biochem. Biophys.*, 393(2):222-235 (2001).
Reid et al., "Studies on the Fermentation of Tobacco 1. The Microflora of Cured and Fermenting Cigar-leaf Tobacco," Bulletin 356, Pennsylvania Agricultural Experiment Station, State College, PA, 18 pages (1938).
Rodermel et al., "Nuclear-Organelle Interactions: Nuclear Antisense Gene Inhibits Ribulose Biphosphate Carboxylase Enzyme Levels in Transformed Tobacco Plants," *Cell*, 55:673-681(1988).
Rohr et al., "Tandem inverted repeat system for selection of effective transgenic RNAi strains of *Chlamydomonas*," *Plant J.* 40:611-621 (2004).
Salehuzzaman et al., "Isolation and characterization of a cDNA encoding granule-bound starch synthase in cassava (*Afanihot esculenta* Crantz) and its antisense expression in potato," *Plant Mol. Biol*, 23(5):947-62(1993).
Schenk et al., "Coordinated plant defense responses in *Arabidopsis* revealed by microarray analysis,"*PNAS*, 97(21):11655-11660 (2000).
Schnable et al., "Genetic recombination in plants," *Curr. Opin. Plant Biol.*, 1:123-129 (1998).
Schopfer et al., "Identification of elicitor-induced cytochrome P450s of soybean (*Glycine max* L.) using differential display of mRNA," *Mol. Gen. Genet*., 258:315-322(1998).
Seal et al., "Isolation of a *Pseudomonas solanacearum*-Specific DNA Probe by Subtraction Hybridization and Construction of Species-Specific Oligonucleotide Primers for Sensitive Detection by the Polymerase Chain Reaction," *Appl. Environ. Microbiol.*, 58(2):3751-3758 (1992).
Sequence 6912f1 obtained from the Internet at http://mrg.pscsiken.go.ip/nicotiana/menu/069.html on Dec. 6, 2007, 1 page.
Shah et al., "Expression of Silent Mutations in Disease Phenotype," Abstract for presentation at 11th International Congress of Human Genetics, 1 page, (2006).
Shen et al., "Resistance Gene Candidates Identified by PCR with Degenerate Oligonucleotide Primers Map to Clusters of Resistance Genes in Lettuce," *Molecular Plant-Microbe Interactions*, 11(8):815-823 (1998).
Shew et al. (Eds.), "Compendium of Tobacco Diseases," published by American Phytopathology Society, 99 pages (1991).
Siminszky et al., "Conversion of nicotine to nornicotine in *Nicotiana tabacum* is mediated by CYP82E4, a cytochrome P450 monooxygenase," *PNAS*, 102(41):14919-14924 (2005).
Sinvany-Villalobo et al., "Expression in Multigene Families. Analysis of Chloroplast and Mitochondrial Proteases," *Plant Physiol*, 135:1336-1345 (2004).
Skarnes, "Entrapment Vectors: A New Tool for Mammalian Genetics," *Bio/Technology*, 8:827-831 (1990).
Smith et al., "Comparison of Biosequences," *Adv. Appl. Math.*, 2:482-489 (1981).
Smith et al., "Total silencing by intron-spliced hairpin RNAs," *Nature*, 407:319-320 (2000).
Spradling et al., "Gene disruptions using P transposable elements: An integral component of the *Drosophila* genome project," *PNAS*, 92:10824-10830 (1995).
Stalberg et al., "Deletion analysis of a 2S seed storage protein promoter of *Brassica napus* in transgenic tobacco," *Plant Mol. Biol.*, 23:671-683 (1993).
Sundaresan et al., "Patterns of gene action in plant development revealed by enhancer trap and gene trap transposable elements," *Genes Dev.*, 9:1797-1810 (1995).
Sureka et al., "Positive Feedback and Noise Activate the Stringent Response Regulator Rel in Mycobacteria," *PLoS One*, 3(3):d 771 (2008).
Takeda et al., "Differentiation between Wild and Vaccine-Derived Strains of Poliovirus by Stringent Microplate Hybridization of PCR Products," *J Clin. Microbial.*, 32:202-204 (1994).
Takemoto et al., "Molecular Cloning of a Defense-Response-Related Cytochrome P450 Gene from Tobacco," *Plant Cell Physiol.*, 40(12):1232-1242 (1999).
Takken et al. "A functional cloning strategy, based on a binary PYX-expression vector, to isolate HR-inducing cDNAs of plant pathogens." *The Plant Journal*, 24(2): 275-283 (2000).
Tang et al., "Using RNAi to improve plant nutritional value: from mechanism to application," *TRENDS in Biotechnology*, 22(9):463-469 (2004).
Tavernarakis et al., "Heritable and inducible genetic interference by double-stranded RNA encoded by transgenes," *Nat. Genet.*, 24:180-183 (2000).
Temple et al., "Modulation of glutamine synthetase gene expression in tobacco by the introduction of an alfalfa glutamine synthetase gene

(56) References Cited

OTHER PUBLICATIONS in sense and antisense orientation: molecular and biochenlical analysis," *Mol Gen Genet*, 236(2-3):315-25 (1993).
Thomas et al., "Size constraints for targeting post-transcriptional gene silencing and for RNA directed methylation in *Nicotiana benthamiana* using a potato virus X vector," *Plant J.*,25(4):417-425 (2001).
Thornton et al., "From structure to function: Approaches and limitations," *Nature Structural Biology, StructuralGenomics Supplement*, pp. 991-994 (2000).
Till et al., "Discovery of induced point mutations in maize genes by Tilling," *BMC Plant Biology*, 4:12 (2004).
Toscano et al., "A silent mutation (2939G>A, exon 6; *CYP2D6*59*) leading to impaired expression and function of CYP2D6," *Pharmacogenet. Genomics*, 16(10):767-770 (2006).
Travella, et al. "RNA Interference-Based Gene Silencing as an Efficient Tool for Functional Genomics in Hexaploid Bread Wheat." *Plant Physiology*, 142:6-20 (2006).
Trevanion et al., "NADP-Malate Dehydrogenase in the C4 Plant *Flaveria bidentis*," *Plant Physiol*, 113(4):1153-1165 (1997).
Turner et al., "Post-transcriptional gene-silencing and RNA interference: genetic immunity, mechanisms and applications," *J. Chem. Technol. Biotechnol.*, 75:869-882 (2000).
United States, "Tobacco in the United States," Miscellaneous Publication No. 867, U.S. Dept. of Agriculture, Agricultural Marketing Service, 27 pages (1979).
Vaistij et al., "Spreading of RNA Targeting and DNA Methylation in RNA Silencing Requires Transcription of the Target Gene and a Putative RNA-Dependent RNA Polymerase," *Plant Cell*, 14:857-867 (2002).
Van der Krol et al., "An anti-sense chalcone synthase gene in transgenic plants inhibits flower pigmentation," *Nature*, 333:866-869 (1988).
Van der Krol et al., "Antisense genes in plants: an overview," *Gene*, 72:45-50 (1988).
Vaucheret et al., "Post-transcriptional gene silencing in plants,"*J.Cell Sci.*, 114:3083-3091 (2001).
Veena et al., "Glyoxalase I from *Brassica juncea*: molecular cloning, regulation and its overexpression confer tolerance in transgenic tobacco under stress," *Plant Journal*, 17(4):385-395 (1999).
Verdaguer et al., "Functional organization of the cassava vein mosaic virus (CsVMV) promoter," *Plant Mol. Biol.*, 37(6):1055-1067 (1998).
Verkerk, "Chimerism of the tomato plant after seed irradiation with fast neutrons," *Neth. J. Agric. Sci.*, 19:197-203 (1971).
Voss et al., "The role of enhancers in the regulation of cell-type-specific transcriptional control," *Trends Biochem. Sci.*, 11(7):287-289 (1986).
Wang et al., "Suppression of a P450 hydroxylase gene in plant trichome glands enhances natural product-based aphid resistance," *Nat. Biotechnol.*, 19:371-374 (2001).
Wang et al., "Isolation and characterization of the *CYP71D16* trichome-specific promoter from *Nicotania tabacum* L," *J Exp. Botany*, 53(376):1891-1897 (2002).
Wang et al., "Elucidation of the functions of genes central to diterpene metabolism in tobacco trichomes using posttranscriptional gene silencing," *Planta*, 216:686-691 (2003).
Waterhouse et al., "Virus resistance and gene silencing in plants can be induced by simultaneous expression of sense and antisense RNA," *PNAS*, 95:13959-13964 (1998).
Weigel et al., "A developmental switch sufficient for flower initiation in diverse plants," *Nature*, 377:495-500 (1995).
Weising et al., "Foreign Genes in Plants: Transfer, Structure, Expression, and Applications," *Ann. Rev. Genetics*, 22:421-477 (1988).
Werck-Reichhart et al., "Cytochromes P450: a success story," *Genome Biology*, 1(6):reviews3003.1-3003.9 (2000).
Werck-Reichhart et al., "Cytochromes P450," The *Arabidopsis* Book, American Society of Plant Biologists, 28 pages (2002).
Wemsman et al., "Time and site of nicotine conversion in tobacco," *Tobacco Science*, 167(22):226-228 (1968).

Wemsman et al., "Relative Stability of Alleles at the Nicotine Conversion Locus of Tobacco," *Tobacco Science*,14:34-36 (1970).
Wemsman et al., "Chapter Seventeen: Tobacco." *Cultivar Development. Crop Species.*, W. H. Fehr (ed.), MacMillan Publishing Go., Inc., New York, N.Y., pp. 669-698 (1987).
Wesley et al., "Construct design for efficient, effective and high-throughput gene silencing in plants," *The Plant Journal*, 27(6): 581-590 (2001).
Wetmur, "DNA Probes: Applications ofthe Principles ofNucleic Acid Hybridization" *Critical Reviews in Bio. and Mol. Biol.*, 26:227-259, (1991).
Whitbred et al., "Molecular Characterization of *CYP73A9* and *CYP82A1* P450 Genes Involved in Plant Defense in Pea," *Plant Physiol.*, 124:47-58 (2000).
Wu et al. "Herbivory Rapidly Activates MAPK Signaling in Attacked and Unattacked Leaf Regions but Not between Leaves of *Nicotiana attenuata*." *The Plant Cell*, 19:1096-1122 (2007).
Xiong et al., "Different effects on ACC oxidase gene silencing triggered by RNA interference in transgenic tomato," *Plant Cell*, 23:639-646 (2004).
Xu et al. "Computational Estimation and Experimental Verification of Off-Target Silencing during Posttranscriptional Gene Silencing in Plants," *Plant Physiology*, 142:429-440 (2006).
Xu et al., "Biochemical and molecular characterizations of nicotine demethylase in tobacco," *Physiologia Plantarum*, 129(2):307-319 (2007).
Zwart et al., "Rapid Screening for Freshwater Bacterial Groups by Using Reverse Line Blot Hybridization," *Appl. Environ. Microbiol.*, 69(10):5875-5883 (2003).
U.S. Appl. No. 60/337,684, filed Nov. 13, 2001, Xu.
U.S. Appl. No. 60/347,444, filed Jan. 11, 2002, Xu.
U.S. Appl. No. 60/363,684, filed Mar. 12, 2002, Xu.
U.S. Appl. No. 60/418,933, filed Oct. 16, 2002, Xu.
U.S. Appl. No. 60/485,368, filed Jul. 8, 2003, Xu.
U.S. Appl. No. 60/503,989, filed Sep. 18, 2003, Xu.
U.S. Appl. No. 60/566,235, filed Apr. 29, 2004, Xu.
U.S. Appl. No. 60/607,357, filed Sep. 3, 2004, Xu.
U.S. Appl. No. 60/646,764, filed Jan. 25, 2005, Xu.
U.S. Appl. No. 60/665,097, filed Mar. 24, 2005, Xu.
U.S. Appl. No. 60/664,451, filed Mar. 24, 2005, Xu.
Adams et al., "Genes duplicated by polyploidy show unequal contributions to the transcriptome and organ-specific reciprocal silencing," *PNAS*, 100(8):4649-4654 (2003).
Allen et al., "RNAi-mediated replacement of morphine with the nonnarcotic alkaloid reticuline in opium poppy," *Nature Biotechnology*, 22(12):1559-1566 (2004).
Alonso et al., "A *Hox* gene mutation that triggers nonsense-mediated RNA decay and affects alternative splicing during *Drosophila* development," *Nucleic Acids Research*, 31(14):3873-3880 (2003).
Arciga-Reyes et al., "UPF1 is required for nonsense-mediated mRNA decay (NMD) and RNAi in *Arabidopsis*" *The Plant Journal*, 47:480-489 (2006).
Arndt et al., "Colocalization of antisense RNAs and ribozymes with their target mRNAs," *Genome*, 40:785-797 (1997).
ARS-GRIN: PI 551280, "*Nicotiana tabacum*," http://www.ars-grin.gov/cgi-bin/npgs/acc/display.pl?1446216, accessed Feb. 2009).
Bak et al., "Transgenic Tobacco and *Arabidopsis* Plants Expressing the Two Multifunctional *Sorghum* Cytochrome P450 Enzymes, CYP79A1 and CYP71E1, Are Cyanogenic and Accumulate Metabolites Derived from Intermediates in Dhurrin Biosynthesis," *Plant Physiol.*, 123:1437-1448 (2000).
Bartoszewski et al., "Cloning of a Wound Inducible *Lycopersicon esculentum* Cytochrome P450 Gene and Lack of Regeneration of Transgenic Plants with Sense or Antisense Constructs," *J.AmSoc. Hort.Sci*, 127(4):535-539 (2002).
Baseggio et al., "Size and genomic location of the pMGA multigene family of *Mycoplasma gallisepticum*," *Microbiology*, 142:1429-1435 (1996).
Batard et al., "Increasing Expression of P450 and P450-Reductase Proteins from Monocots in Heterologous Systems," *Arch. Biochem. Biophys.*, 379:161-169 (2000).
Baulcombe, "Fast Forward Genetics Based on Virus-Induced Gene Silencing," *Current Opinion in PlantBiology*, 2:109-113 (1999).

(56) References Cited

OTHER PUBLICATIONS

Bolitho et al., "Antisense apple ACC-oxidase RNA reduces ethylene production in transgenic tomato fruit," *Plant Science*, 122:91-99 (1997).
Bosher et al., "RNA interference: genetic wand and genetic watchdog," *Nat. Cell Biol.*, 2:E31-E36 (2000).
Bosl et al., "The role of noise and positive feedback in the onset of autosomal dominant diseases," *BMC Systems Biology*,4:1-15 (2010).
Boyette et al., "Results of year 2000 TSNA sampling program in flue-cured tobacco," *Recent Advances in Tobacco Science*, 27:17-22 (2001).
Branch, "A good antisense molecule is hard to t1nd," *TIES*, 23:45-50 (1998).
Brignetti et al., "Viral pathogenicity determinants are suppressors of transgene silencing in *Nicotiana benthamiana*," *EMBO J.*, 17(22):6739-6746 (1998).
Burns et al., "Large-scale analysis of gene expression, protein localization, and gene disruption in *Saccharomyces cerevisiae*," *Genes Dev.*, 8:1087-1105 (1994).
Burton et al., Changes in Chemical Composition of Burley Tobacco During Senescence and Curing. 2. Acylated Pyridine Alkaloids, *American Chemical Society*, pp. 579-583 (1988).
Burton et al., "Distribution of Tobacco Constituents in Tobacco Leaf Tissue. 1. Tobacco-Specific Nitrosamines, Nitrate, Nitrite, and Alkaloids," *J. Agric. Food Chem.*, 40:1050-1055 (1992).
Burton et al., "Changes in Chemical Composition of Burley Tobacco during Senescence and Curing. 2. Acylated Pyridine Alkaloids," *J .Agric. Food Chem.*, 38(3):579-584 (1998).
Bush et al., "Formation of tobacco-specific nitrosamines in air-cured tobacco," *Rec. Adv. Tob. Sci*, 27:23-46 (2001).
Byers et al., "Killing the messenger: new insights into nonsense-mediated mRNA decay" *The Journal of Clinical Investigation*, 109(1):3-6 (2002).
Byzova et al., "Transforming petals into sepaloid organs in *Arabidopsis* and oilseed rape: implementation of the hairpin RNA-mediated gene silencing technology in an organ-specific manner," *Planta*, 218:379-387 (2004).
Callis et al., "Introns increase gene expression in cultured maize cells," *Genes and Dev.*, 1:1183-1200 (1987).
Carron et al., "Genetic modification of condensed tannin biosynthesis in *Lotus comiculatus*. 1. Heterologous antisense dihydroflavonol reductase down-regulates tannin accumulation in "hairy roof" cultures," *Theoretical and Applied Genetics*, 87(8): 1006-1015 (1994).
Caruthers, "Chapter 1: New Methods for Chemically Synthesizing Deoxyoligonucleotides," Methods of DNA and RNA Sequencing, Weissman (ed.), Praeger Publishers, New York, pp. 1-22 (1983).
Chai et al., "Reducing the maize amylopectin content through RNA interference manipulation," *Zhi Wu Sheng Li Yu Fen Zi Sheng Wu Xue Xue Buo*, 31:625-630 (2005) (English Abstract only).
Chakrabarti et al., "Inactivation of the cytochrome P450 gene *CYP82E2* by degenerative mutations was a key event in the evolution of the alkaloid profile of modem tobacco," *New Phytologist*, 175:565-574 (2007).
Chakrabarti et al., "CYP82E4-mediated nicotine to nomicotine conversion in tobacco is regulated by a senescence-specific signaling pathway," *Plant Mol. Biol.*, 66: 415-427 (2008).
Chang et al., "Predicting and Testing Physical Locations of Genetically Mapped Loci on Tomato Pachytene Chromosome," *Genetics*, 176:2131-2138 (2007).
Chao et al., "A silent mutation induces exon skipping in the phenylalanine hydroxylase gene in phenylketonuria," *Hum. Genet.*, 108:14-19 (2001).
Chappell, "Biochemistry and Molecular Biology of the Isoprenoid Biosynthetic Pathway in Plants," *Annu. Rev. Plant Physiol. Plant Mol. Biol.*, 46:521-547(1995).
Chapple, "Molecular-Genetic Analysis of Plant Cytochrome P450-Dependent Monooxygenases," *Annu. Rev. Plant Physiol. Plant Mol. Biol.*, 49:311-343 (1998).

Chelvarajan et al., Study of Nicotine Demethylation in *Nicotiana otophora, J. Agric. Food Chem.*, 41:858-862 (1993).
Cheung et al., "A Floral Transmitting Tissue-Specific Glycoprotein Attracts Pollen Tubes and Stimulates Their Growth," *Cell*, 82:383-393 (1995).
Chintapakorn, et al., "Antisense-Mediated Down-Regulation of Putrescine N-Methyltransferase Activity in Transgenic *Nicotiana tabacum* L. can Lead to Elevated Levels of Anatabine at the Expense of Nicotine," *Plant Molecular Biology*, 53:87-105 (2003).
Cho et al., "Transcriptome Analysis and Physical Mapping of Barley Genes in Wheat-Barley Chromosome Addition Lines," *Genetics*, 172:1277-1285 (2006).
Chou et al., "Chromosome Rearrangements in *Arabidopsis thaliana* Generated Through Cre-lox Site Specific Recombination," Plant and Animal Genome VII Conference, Abstract No. P133, 1 page (1999).
Chuang et al., "Specific and heritable genetic interference by double-stranded RNA in *Arabidopsis thaliana*," *PNAS*, 97(9):4985-4990 (2000).
Cogoni et al., "Post-transcriptional gene silencing across kingdoms," *Curr. Opin. Genet. Dev.*, 10:638-643 (2000).
Colbert et al., "High-throughput screening for induced point mutations," *Plant Physiology*, 126:480-484 (2001).
Collier et al., "A Method for Specific Amplification and PCR Sequencing of Individual Members of Multigene Families: Application to the Study of Steroid 21-Hydroxylase Deficiency," *PCR Methods and Applications*, 1:181-186 (1992).
Colliver et al., "Differential modification of flavonoid and isoflavonoid biosynthesis with an antisense chalcone synthase construct in transgenic *Lotus comiculatus*," *Plant Mol. Biol.*, 35(4):509-522 (1997).
Crookshanks et al., "The potato tuber transcriptome: analysis of 6077 expressed sequence tags," *FEBS Lett.*, 506:123-126 (2001).
Davuluri et al., "Fruit-specific RNAi-mediated suppression of DET1 enhances carotenoid and favonoid content in tomatoes," *Nat. Biotechnol.*, 23:890-895 (2005).
Dekeyser et al., Transient Gene Expression in Intact and Organized Rice Tissues, *Plant Cell*, 2:591-602 (1990).
Dewey et al., Meeting Abstract dated Sep. 27, 2005, 1 page.
Dewey et al., Power point presentation titled "Functional characterization of the nicotine N-Demethylase gene of tobacco," Philip Morris USA, 21 pages, 2006.
Donato et al., "Fluorescence-Based Assays in Intact Cells Expressing Individual Activities for Screening Nine Cytochrome P450 (P450) Human P450 Enzymes," *Drug Metab. Dispos.*, 32(7):699-706 (2004).
D'Souza et al., "Missense and silent tau gene mutations cause frontotemporal dementia with parkinsonism-chromosome 17 type, by affecting multiple alternative RNA splicing regulatory elements" *PNAS*, 96:5598-5603 (1999).
EBI Accession AV557806, dated Jun. 16, 2000, 2 pages.
Einset, "Differential expression of antisense in regenerated tobacco plants transformed with an antisense version of a tomato ACC oxidase gene," *Plant Cell Tissue and Organ Culture*, 46(2): 137-141 (1996).
Elkind et al., "Abnormal plant development and down-regulation of phenylpropanoid biosynthesis in transgenic tobacco containing a heterologous phenylalanine ammonia-lyase gene," *PNAS*, 87(22):9057-61 (1990).
EMBL Database Report for Accession No. EU182719, Dec. 2, 2007 (XP002511576).
Escobar et al., "RNAi-mediated oncogene silencing confers resistance to crown gall tumorigenesis," *PNAS*, 98: 13437-13442 (2001).
European Search Report completed on Feb. 10, 2010, in European Application No. EP 07 86 5628, 4 pages.
European Search Report completed on Mar. 31, 2011, in European Application No. EP 10 01 5540, 8 pages.
Falcon-Perez et al., "Functional Domain Analysis of the Yeast ABC Transporter Ycflp by Site-directed Mutagenesis," *J. Biol. Chem.*, 274(33):23584-23590 (1999).
Fang et al., "Multiple cis regulatory elements for maximal expression of the cauliflower mosaic virus 35S promoter in transgenic plants," *Plant Cell*, 1:141-150 (1989).

(56) References Cited

OTHER PUBLICATIONS

Fannin et al., "Nicotine demethylation in *Nicotiana*," *Med. Sci. Res.*, 20:807-808 (1992).
Faske et al., "Transgenic Tobacco Plants Expressing Pea Chloroplast Nmdh eDNA in Sense and Antisense Orientation," *Plant Physiol*, 115(2): 705-715 (1997).
Fedoroff et al., "Cloning of the bronze locus in maize by a simple and generalizable procedure using the transposable controlling element Activator (Ac)," *PNAS*, 81 :3825-3829 (1984).
Fire et al., "Potent and specific genetic interference by double-stranded RNA in *Caenorhabditis elegans*," *Nature*, 391:806-811 (1998).
Force et al., "Preservation of Duplicate Genes by Complementary, Degenerative Mutations," *Genetics*, 151:1531-1545 (1999).
Forsthoefel et al., "T-DNA Insertion Mutagenesis in *Arabidopsis*: Prospects and Perspectives," *Aust. J. Plant Physiol.*, 19:353-366 (1992).
Frank et al., "Cloning of Wound-Induced Cytochrome P450 Monooxygenases Expressed in Pea," *Plant Physiol.*, 110:1035-1046 (1996).
Freeman et al., "Quantitative RT-PCR: Pitfalls and Potential," *BioTechniques*, 26:112-125 (1999).
Fromm et al., "An octopine synthase enhancer element directs tissue-specific expression and binds ASF-1, a factor from tobacco nuclear extracts," *Plant Cell*, 1:977-984 (1989).
Gavilano, "Isolation, Cloning and Characterization of Novel Tobacco Cytochrome P450 Genes Involved in Secondary Metabolism," Plant Biology Meeting, American Society of Plant Biologists, Abstract No. 992, 1 page (2004).
Gavilano et al. "Genetic Engineering of *Nicoticma tabacum* for Reduced Nomicotine Content" *J. Agric. Food Chem.*, 54:9071-9078 (2006).
Gavilano et al., "Functional Analysis of Nicotine Demethylase Genes Reveals Insights into the Evolution of Modem Tobacco," *J. Biol. Chem.*, 282:249-256 (2007).
Gavilano et al., "Isolation and Characterization of the Cytochrome P450 Gene CYP82E5v2 that Mediates Nicotine to Nornicotine Conversion in the Green Leaves of Tobacco," *Plant Cell Physiol.*, 48(11):1567-1574 (2007).
GenBank Accession No. CAA64635, dated Sep. 12, 1996, 2 pages.
GenBank Accession No. BAA35080, dated Sep. 26, 2000, 2 pages.
GenBank Accession No. AAK62347, dated Jun. 14, 2001, 2 pages.
GenBank Accession No. AAK62343, dated Feb. 11, 2002, 2 pages.
GenBank Accession No. AAK62346, dated Feb. 11, 2002, 2 pages.
GenBank Accession No. AEK08729 dated Feb. 23, 2005, 2 pages.
GenBank Accession No. AAK62342, Sep. 20, 2005, 2 pages.
GenBank Accession No. ABA07804, dated Oct. 13, 2005, 2 pages.
GenBank Accession No. ABA07805, dated Oct. 13, 2005, 2 pages.
GenBank Accession No. ABA07807, dated Oct. 13, 2005, 2 pages.
GenBank Accession No. DQ131885, dated Oct. 13, 2005, 2 pages.
GenBank Accession No. DQ131886, dated Oct. 13, 2005, 2 pages.
GenBank Accession No. DQ131888, dated Oct. 13, 2005, 2 pages.
GenBank Accession No. DQ219341, dated Oct. 1, 2006, 2 pages.
GenBank Accession No. DQ219342, dated Oct. 1, 2006, 2 pages.
GenBank Accession No. DQ219343, dated Oct. 1, 2006, 2 pages.
Notification of Transmittal of the International Search Report and the Written Opinion of the International Searching Authority, or the Declaration in correspondence PCT Application No. PCT/US2012/026864 mailed May 4, 2012 (13 pages).
Gavilano et al., "Genetic Engineering of *Nicotiana tabacum* for Reduced Nornicotine Content" *J. Agric. Food Chem.* (2006) 54:9071-9078.
Julio et al., "Reducing the content of nornicotine in tobacco via targeted mutation breeding," *Mol. Breeding* (2008) 21:369-381.
Lewis et al., "Three nicotine demethylase genes mediate nornicotine biosynthesis in *Nicotiana tabacum* L.: Functional characterization of the *CYP82E10* gene," *Phytochemistry* (2010) 71:1988-1998.
ARS-GRIN: PI 543792, "*Nicotiana tabacum*—'TN 90'" http://www.ars-grin.gov/cgi-bin/npgs/acc/display.pl?1438728, Retrieved Date: Sep. 2013 (2 pp).
Horlow et al., "Transfer of cytoplasmic male sterility by spontaneous androgenesis in tobacco (*Nicotiana tabacum* L.)" *Euphytica* 66:45-53 (1993).
Notification Concerning Transmittal of International Preliminary Report on Patentability in corresponding PCT Application No. PCT/US2012/026864 mailed Sep. 12, 2013 (8 pp).
Notification of Transmittal of The International Search Report and The Written Opinion of The International Searching Authority, or The Declaration, PCT/US2014/011035, Apr. 23, 2014, 11 pages.
Jack et al., "Relative Stability of Nicotine to Nornicotine Conversion in Three Burley Cultivars," 18 pages, 36 slides (basis for Jack et al., published in *COREST* Congress Abstract AP2, Kyoto (2004) Agro Phyto Groups; 32 pages (unpaginated, abstract appearing on p. 11)).
Mann et al., "Inheritance of the Conversion of Nicotine to Nornicotine in Varieties of *Nicotiana tabacum* L. and Related Amphiploids," *Crop Sci.*, 4:349-53 (1964).
Bindler et al., "CORESTA Task Force Genetically Modified Tobacco: Detection Methods," 41 pages, 1999.
Saunders et al., "The Use of AFLP Techniques for DNA Fingerprinting in Plants," CEQ 2000XL, Beckman Coulter, 8 pages, 2001.
Slater et al., Plant biotechnology: the genetic manipulation of plants 39 (Oxford University Press 2008) Chapter 2, pp. 37-53, 2nd ed.
T. David Reed, "Curing Tobacco," 2008 Flue-cured Tobacco Production Guide, pp. 61-64.
Ruiz et al., "Nicotine-free and salt-tolerant tobacco plants obtained by grafting to salinity-resistant rootstocks of tomato," Physiologia Plantarum, vol. 124, No. 4, Aug. 1, 2005, pp. 465-475.
Chen et al., "Toxicological analysis of low-nicotine and nicotine-free cigarettes," Toxicology, vol. 249, No. 2-3, Jul. 30, 2008, 19 pages.
Invitation to Pay Additional Fees, PCT/US2014/019381, Jun. 23, 2014, 8 pages.

\* cited by examiner

SEQUENCE LISTING

```
<160> NUMBER OF SEQ ID NOS: 8

<210> SEQ ID NO 1
<211> LENGTH: 1751
<212> TYPE: DNA
<213> ORGANISM: Nicotiana tabacum

<400> SEQUENCE: 1
aaggaagttg ccgatagtta tattctcaac ttcttatcta aaaatccata atgctttctc      60
ccatagaagc cattgtagga ctagtaacct tcacatttct cttcttcttc ctatggacaa     120
aaaaatctca aaaaccttca aaaccottac caccgaaaat ccccggagga tggccggtaa     180
tcggccatct tttccacttc aatgacgacg gcgacgaccg tccattagct cgaaaactcg     240
gagacttagc tgacaaatac ggccccgttt tcactttttcg gctaggcctt ccccttgtct     300
tagttgtaag cagttacgaa gctgtaaaag actgtttctc tacaaatgac gccatttttt     360
ccaatcgtcc agcttttctt tacggcgatt accttggcta caataatgcc atgctatttt     420
tggccaatta cggaccttac tggcgaaaaa atcgaaaatt agttattcag gaagttctct     480
ccgctagtcg tctcgaaaaa ttcaaacacg tgagatttgc aagaattcaa gcgagcatta     540
agaatttata tactcgaatt gatggaaatt cgagtacgat aaatttaact gattggttag     600
aagaattgaa ttttggtctg atcgtgaaga tgatcgctgg aaaaaattat gaatccggta     660
aaggagatga acaagtggag agatttaaga aagcgtttaa ggattttatg attttatcaa     720 tggagttgt gttatgggat gcatttccaa ttccattatt taaatgggtg gattttcaag     780
ggcatgttaa ggctatgaaa aggacttta aagatataga ttctgttttt cagaattggt     840
tagaggaaca tattaataaa agagaaaaa tggaggttaa tgcagaaggg aatgaacaag     900
atttcattga tgtggtgctt tcaaaaatga gtaatgaata tcttggtgaa ggttactctc     960
gtgatactgt cattaaagca acggtgttta gtttggtctt ggatgcagca gacacagttg    1020
ctcttcacat aaattaggga atggcattat tgataaacaa tcaaaaggcc ttgacgaaag    1080
```

-continued

```
cacaagaaga gatagacaca aaagttggta aggacagatg ggtagaagag agtgatatta      1140
aggatttggt atacctccaa gctattgtta aagaagtgtt acgattatat ccaccaggac      1200
ctttgttagt accacacgaa aatgtagaag attgtgttgt tagtggatat cacattccta      1260
aagggacaag attattcgca aacgtcatga aactgcaacg tgatcctaaa ctctggtctg      1320
atcctgatac tttcgatcca gagagattca ttgctactga tattgacttt cgtggtcagt      1380
actataagta tatcccgttt ggttctggaa gacgatcttg tccagggatg acttatgcat      1440
tgcaagtgga acacttaaca atggcacatt tgatccaagg tttcaattac agaactccaa      1500
atgacgagcc cttggatatg aaggaaggtg caggcataac tatacgtaag gtaaatcctg      1560
tggaactgat aatagcgcct cgcctggcac ctgagcttta ttaaaaccta agatctttca      1620
tcttggttga tcattgtata atactcctaa atggatattc atttaccttt tatcaattaa      1680
ttgtcagtac gagttttttct aatttggtac atttgtaata ataagtaaag aataattgtg      1740
ctaatatata a                                                          1751
```

<210> SEQ ID NO 2
<211> LENGTH: 1554
<212> TYPE: DNA
<213> ORGANISM: Nicotiana tabacum

<400> SEQUENCE: 2

```
atggtttttc cggtagaagc cattgtagga ctagtaaccc ttacacttct cttctacttc       60
ctatggccca aaaatttca atacctcca aaccattac caccgaaaat tcccggaggg       120
tggccggtaa tcggccatct tttctacttc gatgatgacg gcgacgaccg tccattagct      180
cgaaaactcg gagacttagc tgacaaatac ggcccggttt tcactttccg gctaggcctt      240
ccgcttgtgt tagttgtaag cagttacgaa gctgtaaaag actgcttctc tacaaatgac      300 gccatttttct ccaatcgtcc agcttttctt tacggtgaat accttggcta cagtaatgcc      360
atgctatttt tgacaaaata cggaccttat tggcgaaaaa atagaaaatt agtcattcag      420
gaagttctct ctgctagtcg tctcgaaaaa ttgaagcacg tgagatttgg taaaattcaa      480
acgagcatta agagtttata cactcgaatt gatggaaatt cgagtacgat aaatctaact      540
gattggttag aagaattgaa ttttggtctg atcgtgaaaa tgatcgctgg gaaaaattat      600
gaatccggta aaggagatga acaagtggag agatttagga aagcgtttaa ggattttata      660
attttatcaa tggagtttgt gttatgggat gcttttccaa ttccattgtt caaatgggtg      720
gattttcaag gccatgttaa ggccatgaaa aggacattta aggatataga ttctgttttt      780
cagaattggt tagaggaaca tgtcaagaaa agagaaaaaa tggaggttaa tgcacaaggg      840
aatgaacaag atttcattga tgtggtgctt tcaaaaatga gtaatgaata tcttgatgaa      900
ggttactctc gtgatactgt cataaaagca acagtgttta gtttggtctt ggatgctgcg      960
gacacagttg ctcttcacat gaattgggga atggcattac tgataaacaa tcaacatgcc     1020
ttgaagaaag cacaagaaga gatcgataaa aaagttggta aggaaagatg ggtagaagag     1080
agtgatatta aggatttggt ctacctccaa gctattgtta aagaagtgtt acgattatat     1140
ccaccaggac ctttattagt acctcatgaa aatgtagagg attgtgttgt tagtggatat     1200
cacattccta aagggactag actattcgcg aacgttatga aattgcagcg cgatcctaaa     1260
ctctgatcaa atcctgataa gtttgatcca gagagattct tcgctgatga tattgactac     1320
cgtggtcagc actatgagtt tatcccatttt ggttctggaa gacgatcttg tccggggatg     1380
```

```
acttatgcat tacaagcgga acacctaaca atagcacatt tgatccaggg tttcaattac    1440
aaaactccaa atgacgagcc cttggatatg aaggaaggtg caggattaac tatacgtaaa    1500
gtaaatcctg tagaagtgac aattacggct cgcctggcac ctgagcttta ttaa          1554
```

<210> SEQ ID NO 3
<211> LENGTH: 328
<212> TYPE: PRT
<213> ORGANISM: Nicotiana tabacum

<400> SEQUENCE: 3

```
Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
                20                  25                  30

Leu Pro Pro Lys Ile Pro Gly Gly Trp Pro Val Ile Gly His Leu Phe
            35                  40                  45

His Phe Asn Asp Asp Gly Asp Asp Arg Pro Leu Ala Arg Lys Leu Gly
        50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
                100                 105                 110

Asp Tyr Leu Gly Tyr Asn Asn Ala Met Leu Phe Leu Ala Asn Tyr Gly
            115                 120                 125

Pro Tyr Trp Arg Lys Asn Arg Lys Leu Val Ile Gln Glu Val Leu Ser
130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Lys Lys Ala Phe Lys Asp Phe Met Ile Leu Ser Met
210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu His Ile Asn Lys Arg Glu
            260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Gly Glu Gly Tyr Ser Arg
290                 295                 300

Asp Thr Val Ile Lys Ala Thr Val Phe Ser Leu Val Leu Asp Ala Ala
305                 310                 315                 320

Asp Thr Val Ala Leu His Ile Asn
                325
```

<210> SEQ ID NO 4

<211> LENGTH: 421
<212> TYPE: PRT
<213> ORGANISM: Nicotiana tabacum

<400> SEQUENCE: 4

```
Met Val Phe Pro Val Glu Ala Ile Val Gly Leu Val Thr Leu Thr Leu
1               5                   10                  15

Leu Phe Tyr Phe Leu Trp Pro Lys Lys Phe Gln Ile Pro Ser Lys Pro
            20                  25                  30

Leu Pro Pro Lys Ile Pro Gly Gly Trp Pro Val Ile Gly His Leu Phe
        35                  40                  45

Tyr Phe Asp Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
            100                 105                 110

Glu Tyr Leu Gly Tyr Ser Asn Ala Met Leu Phe Leu Thr Lys Tyr Gly
        115                 120                 125

Pro Tyr Trp Arg Lys Asn Arg Lys Leu Val Ile Gln Glu Val Leu Ser
    130                 135                 140

Ala Ser Arg Leu Glu Lys Leu Lys His Val Arg Phe Gly Lys Ile Gln
145                 150                 155                 160

Thr Ser Ile Lys Ser Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Arg Lys Ala Phe Lys Asp Phe Ile Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Val Lys Lys Arg Glu
            260                 265                 270

Lys Met Glu Val Asn Ala Gln Gly Asn Glu Gln Asp Phe Ile Asp Val
        275                 280                 285

Val Leu Ser Lys Met Ser Asn Glu Tyr Leu Asp Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Glu Ile Asp Lys Lys Val
            340                 345                 350

Gly Lys Glu Arg Trp Val Glu Glu Ser Asp Ile Lys Asp Leu Val Tyr
        355                 360                 365

Leu Gln Ala Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
```

```
            385                 390                 395                 400
His Ile Pro Lys Gly Thr Arg Leu Phe Ala Asn Val Met Lys Leu Gln
                405                 410                 415
Arg Asp Pro Lys Leu
        420

<210> SEQ ID NO 5
<211> LENGTH: 1751
<212> TYPE: DNA
<213> ORGANISM: Nicotiana tabacum

<400> SEQUENCE: 5
aaggaagttg ccgatagtta tattctcaac ttcttatcta aaaatccata atgctttctc      60
ccatagaagc cattgtagga ctagtaacct tcacatttct cttcttcttc ctatggacaa     120
aaaaatctca aaaccttca aaacccttac caccgaaaat ccccggagga tggccggtaa     180
tcggccatct tttccacttc aatgacgacg gcgacgaccg tccattagct cgaaaactcg     240
gagacttagc tgacaaatac ggccccgttt tcacttttcg gctaggcctt ccccttgtct     300
tagttgtaag cagttacgaa gctgtaaaag actgtttctc tacaaatgac gccattttt     360 ccaatcgtcc agcttttctt tacgcgatt accttggcta caataatgcc atgctatttt     420
tggccaatta cggaccttac tggcgaaaaa atcgaaaatt agttattcag gaagttctct     480
ccgctagtcg tctcgaaaaa ttcaaacacg tgagatttgc aagaattcaa gcgagcatta     540
agaatttata tactcgaatt gatggaaatt cgagtacgat aaatttaact gattggttag     600
aagaattgaa ttttggtctg atcgtgaaga tgatcgctgg aaaaaattat gaatccggta     660
aaggagatga acaagtggag agatttaaga agcgtttaa ggattttatg attttatcaa     720 tggagttgt gttatgggat gcatttccaa ttccattatt taaatgggtg gattttcaag     780
ggcatgttaa ggctatgaaa aggactttta agatataga ttctgttttt cagaattggt     840
tagaggaaca tattaataaa agagaaaaaa tggaggttaa tgcagaaggg aatgaacaag     900
atttcattga tgtggtgctt tcaaaaatga gtaatgaata tcttggtgaa ggttactctc     960
gtgatactgt cattaaagca acggtgttta gtttggtctt ggatgcagca gacacagttg    1020
ctcttcacat aaattgggga atggcattat tgataaacaa tcaaaaggcc ttgacgaaag    1080
cacaagaaga gatagacaca aaagttggta aggacagatg ggtagaagag agtgatatta    1140
aggatttggt atacctccaa gctattgtta agaagtgtt acgattatat ccaccaggac    1200
ctttgttagt accacacgaa aatgtagaag attgtgttgt tagtggatat cacattccta    1260
aagggacaag attattcgca aacgtcatga aactgcaacg tgatcctaaa ctctggtctg    1320
atcctgatac tttcgatcca gagagattca ttgctactga tattgacttt cgtggtcagt    1380
actataagta tatcccgttt ggttctggaa gacgatcttg tccagggatg acttatgcat    1440
tgcaagtgga acacttaaca atggcacatt tgatccaagg tttcaattac agaactccaa    1500
atgacgagcc cttggatatg aaggaaggtg caggcataac tatacgtaag gtaaatcctg    1560
tggaactgat aatagcgcct cgcctggcac ctgagcttta ttaaaaccta agatctttca    1620
tcttggttga tcattgtata atactcctaa atggatattc atttaccttt tatcaattaa    1680
ttgtcagtac gagttttttct aatttggtac atttgtaata ataagtaaag aataattgtg    1740
ctaatatata a                                                          1751

<210> SEQ ID NO 6
<211> LENGTH: 1554
```

<212> TYPE: DNA
<213> ORGANISM: Nicotiana tabacum

<400> SEQUENCE: 6

```
atggttttc cggtagaagc cattgtagga ctagtaaccc ttacacttct cttctacttc        60
ctatggccca aaaatttca aataccttca aaaccattac caccgaaaat tcccggaggg       120
tggccggtaa tcggccatct tttctacttc gatgatgacg gcgacgaccg tccattagct       180
cgaaaactcg gagacttagc tgacaaatac ggcccggttt tcactttccg gctaggcctt       240
ccgcttgtgt tagttgtaag cagttacgaa gctgtaaaag actgcttctc tacaaatgac       300
gccattttct ccaatcgtcc agcttttctt tacggtgaat accttggcta cagtaatgcc       360
atgctatttt tgacaaaata cggaccttat tggcgaaaaa atagaaaatt agtcattcag       420
gaagttctct ctgctagtcg tctcgaaaaa ttgaagcacg tgagatttgg taaaattcaa       480
acgagcatta agagtttata cactcgaatt gatggaaatt cgagtacgat aaatctaact       540
gattggttag aagaattgaa ttttggtctg atcgtgaaaa tgatcgctgg aaaaaattat       600
gaatccggta aggagatga acaagtggag agatttagga aagcgtttaa ggatttatata       660
atttatcaa tggagtttgt gttatgggat gcttttccaa ttccattgtt caatggggtg       720
gattttcaag gccatgttaa ggccatgaaa aggacattta aggatataga ttctgttttt       780
cagaattggt tagaggaaca tgtcaagaaa agagaaaaaa tggaggttaa tgcacaaggg       840
aatgaacaag atttcattga tgtggtgctt tcaaaaatga gtaatgaata tcttgatgaa       900
ggttactctc gtgatactgt cataaaagca acagtgttta gtttggtctt ggatgctgcg       960
gacacagttg ctcttcacat gaattgggga atggcattac tgataaacaa tcaacatgcc      1020
ttgaagaaag cacaagaaga gatcgataaa aaagttggta aggaaagatg ggtagaagag      1080
agtgatatta aggatttggt ctacctccaa gctattgtta agaagtgtt acgattatat       1140
ccaccaggac ctttattagt acctcatgaa aatgtagagg attgtgttgt tagtggatat      1200
cacattccta aagggactag actattcgcg aacgttatga aattgcagcg cgatcctaaa      1260
ctctggtcaa atcctgataa gtttgatcca gagagattct tcgctgatga tattgactac      1320
cgtggtcagc actatgagtt tatcccattt ggttctggaa gacgatcttg tccggggatg      1380
acttatgcat acaagcgga acacctaaca atagcacatt tgatccaggg tttcaattac      1440
aaaactccaa atgacgagcc cttggatatg aaggaaggtg caggattaac tatacgtaaa      1500
gtaaatcctg tagaagtgac aattacggct cgcctggcac ctgagcttta ttaa           1554
```

<210> SEQ ID NO 7
<211> LENGTH: 517
<212> TYPE: PRT
<213> ORGANISM: Nicotiana tabacum

<400> SEQUENCE: 7

```
Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
            20                  25                  30

Leu Pro Pro Lys Ile Pro Gly Gly Trp Pro Val Ile Gly His Leu Phe
        35                  40                  45

His Phe Asn Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80
```

```
Pro Leu Val Leu Val Ser Ser Tyr Glu Ala Val Lys Asp Cys Phe
                85              90              95

Ser Thr Asn Asp Ala Ile Phe Ser Asn Arg Pro Ala Phe Leu Tyr Gly
            100             105             110

Asp Tyr Leu Gly Tyr Asn Asn Ala Met Leu Phe Leu Ala Asn Tyr Gly
            115             120             125

Pro Tyr Trp Arg Lys Asn Arg Lys Leu Val Ile Gln Glu Val Leu Ser
        130             135             140

Ala Ser Arg Leu Glu Lys Phe Lys His Val Arg Phe Ala Arg Ile Gln
145             150             155             160

Ala Ser Ile Lys Asn Leu Tyr Thr Arg Ile Asp Gly Asn Ser Ser Thr
                165             170             175

Ile Asn Leu Thr Asp Trp Leu Glu Glu Leu Asn Phe Gly Leu Ile Val
            180             185             190

Lys Met Ile Ala Gly Lys Asn Tyr Glu Ser Gly Lys Gly Asp Glu Gln
            195             200             205

Val Glu Arg Phe Lys Lys Ala Phe Lys Asp Phe Met Ile Leu Ser Met
        210             215             220

Glu Phe Val Leu Trp Asp Ala Phe Pro Ile Pro Leu Phe Lys Trp Val
225             230             235             240

Asp Phe Gln Gly His Val Lys Ala Met Lys Arg Thr Phe Lys Asp Ile
                245             250             255

Asp Ser Val Phe Gln Asn Trp Leu Glu Glu His Ile Asn Lys Arg Glu
            260             265             270

Lys Met Glu Val Asn Ala Glu Gly Asn Glu Gln Asp Phe Ile Asp Val
            275             280             285

Val Leu Ser Lys Met Ser Asn Glu Tyr Leu Gly Glu Gly Tyr Ser Arg
        290             295             300

Asp Thr Val Ile Lys Ala Thr Val Phe Ser Leu Val Leu Asp Ala Ala
305             310             315             320

Asp Thr Val Ala Leu His Ile Asn Trp Gly Met Ala Leu Leu Ile Asn
                325             330             335

Asn Gln Lys Ala Leu Thr Lys Ala Gln Glu Glu Ile Asp Thr Lys Val
            340             345             350

Gly Lys Asp Arg Trp Val Glu Glu Ser Asp Ile Lys Asp Leu Val Tyr
            355             360             365

Leu Gln Ala Ile Val Lys Glu Val Leu Arg Leu Tyr Pro Pro Gly Pro
        370             375             380

Leu Leu Val Pro His Glu Asn Val Glu Asp Cys Val Val Ser Gly Tyr
385             390             395             400

His Ile Pro Lys Gly Thr Arg Leu Phe Ala Asn Val Met Lys Leu Gln
                405             410             415

Arg Asp Pro Lys Leu Trp Ser Asp Pro Asp Thr Phe Asp Pro Glu Arg
            420             425             430

Phe Ile Ala Thr Asp Ile Asp Phe Arg Gly Gln Tyr Tyr Lys Tyr Ile
            435             440             445

Pro Phe Gly Ser Gly Arg Arg Ser Cys Pro Gly Met Thr Tyr Ala Leu
        450             455             460

Gln Val Glu His Leu Thr Met Ala His Leu Ile Gln Gly Phe Asn Tyr
465             470             475             480

Arg Thr Pro Asn Asp Glu Pro Leu Asp Met Lys Glu Gly Ala Gly Ile
                485             490             495
```

```
Thr Ile Arg Lys Val Asn Pro Val Glu Leu Ile Ile Ala Pro Arg Leu
            500                 505                 510
Ala Pro Glu Leu Tyr
        515

<210> SEQ ID NO 8
<211> LENGTH: 517
<212> TYPE: PRT
<213> ORGANISM: Nicotiana tabacum

<400> SEQUENCE: 8

Met Val Phe Pro Val Glu Ala Ile Val Gly Leu Val Thr Leu Thr Leu
1               5                   10                  15

Leu Phe Tyr Phe Leu Trp Pro Lys Lys Phe Gln Ile Pro Ser Lys Pro
            20                  25                  30

Leu Pro Pro Lys Ile Pro Gly Gly Trp Pro Val Ile Gly His Leu Phe
            35                  40                  45

Tyr Phe Asp Asp Asp Gly Asp Asp Arg Pro Leu Ala Arg Lys Leu Gly
50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
                100                 105                 110

Glu Tyr Leu Gly Tyr Ser Asn Ala Met Leu Phe Leu Thr Lys Tyr Gly
            115                 120                 125

Pro Tyr Trp Arg Lys Asn Arg Lys Leu Val Ile Gln Glu Val Leu Ser
            130                 135                 140

Ala Ser Arg Leu Glu Lys Leu Lys His Val Arg Phe Gly Lys Ile Gln
145                 150                 155                 160

Thr Ser Ile Lys Ser Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
                180                 185                 190

Lys Met Ile Ala Gly Lys Asn Tyr Glu Ser Gly Lys Gly Asp Glu Gln
            195                 200                 205

Val Glu Arg Phe Arg Lys Ala Phe Lys Asp Phe Ile Ile Leu Ser Met
            210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu His Val Lys Lys Arg Glu
                260                 265                 270

Lys Met Glu Val Asn Ala Gln Gly Asn Glu Gln Asp Phe Ile Asp Val
            275                 280                 285

Val Leu Ser Lys Met Ser Asn Glu Tyr Leu Asp Glu Gly Tyr Ser Arg
            290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Glu Ile Asp Lys Lys Val
            340                 345                 350
```

-continued

```
Gly Lys Glu Arg Trp Val Glu Glu Ser Asp Ile Lys Asp Leu Val Tyr
    355                 360                 365

Leu Gln Ala Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
            405                 410                 415

Arg Asp Pro Lys Leu Trp Ser Asn Pro Asp Lys Phe Asp Pro Glu Arg
            420                 425                 430

Phe Phe Ala Asp Asp Ile Asp Tyr Arg Gly Gln His Tyr Glu Phe Ile
        435                 440                 445

Pro Phe Gly Ser Gly Arg Arg Ser Cys Pro Gly Met Thr Tyr Ala Leu
    450                 455                 460

Gln Ala Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
            485                 490                 495

Thr Ile Arg Lys Val Asn Pro Val Glu Val Thr Ile Thr Ala Arg Leu
            500                 505                 510

Ala Pro Glu Leu Tyr
            515
```

TOBACCO INBRED PLANTS NCBEX1F, NCBEX1MS, AND NC EX90

CROSS-REFERENCE TO RELATED APPLICATIONS

This application claims the benefit under 35 U.S.C. §119 of U.S. Provisional Application No. 61/447,443, filed Feb. 28, 2011 and U.S. Provisional Application No. 61/546,573, filed Oct. 13, 2011, each of which is herein incorporated by reference in its entirety, including its respective sequence listing.

INCORPORATION OF SEQUENCE LISTING

The Sequence Listing is hereby incorporated by reference in its entirety, including the file named P33831US02.txt, which is 28,672 bytes in size and was created on Feb. 17, 2012, which is likewise herein incorporated by reference in its entirety.

FIELD OF THE INVENTION

The present invention provides tobacco inbred plants NCBEX1F, NCBEX1MS, and NC EX90. The present invention also provides parts of such plants and products made from those parts. The present invention also includes progeny of the provided plants including hybrids.

BACKGROUND OF THE INVENTION

Tobacco (*Nicotiana tabacum* L.) is an important commercial crop in the United States as well as in other countries. In tobacco plants, N-demethylation of nicotine results in nornicotine, a secondary alkaloid known to be a precursor for formation of N-Nitrosonornicotine ("NNN") in cured leaves. NNN is an undesired component of cured leaves.

The predominant alkaloid found in commercial tobacco varieties is nicotine, typically accounting for 90-95% of the total alkaloid pool. The remaining alkaloid fraction is comprised primarily of three additional pyridine alkaloids: nornicotine, anabasine, and anatabine. Nornicotine is generated directly from nicotine through the activity of the enzyme nicotine N-demethylase. Nornicotine usually represents less than 5% of the total pyridine alkaloid pool, but through a process termed "conversion," tobacco plants that initially produce very low amounts of nornicotine give rise to progeny that metabolically "convert" a large percentage of leaf nicotine to nornicotine. In tobacco plants that have genetically converted (termed "converters"), the great majority of nornicotine production occurs during the senescence and curing of the mature leaf (Wernsman and Matzinger (1968) *Tob. Sci.* 12:226-228). Burley tobaccos are particularly prone to genetic conversion, with rates as high as 20% per generation observed in some cultivars.

During the curing and processing of the tobacco leaf, a portion of the nornicotine is metabolized to the compound NNN, a tobacco-specific nitrosamine (TSNA) that has been asserted to be carcinogenic in laboratory animals (Hecht and Hoffmann (1990) *Cancer Surveys* 8:273-294; Hoffmann et al. (1994) *J. Toxicol. Environ. Health* 41:1-52; Hecht (1998) *Chem. Res. Toxicol.* 11:559-603). In flue-cured tobaccos, TSNAs are found to be predominantly formed through the reaction of alkaloids with the minute amounts of nitrogen oxides present in combustion gases formed by the direct-fired heating systems found in traditional curing barns (Peele and Gentry (1999) "Formation of Tobacco-specific Nitrosamines in Flue-cured Tobacco," CORESTA Meeting, Agro-Phyto Groups, Suzhou, China). Retrofitting these curing barns with heat-exchangers virtually eliminated the mixing of combustion gases with the curing air and dramatically reduced the formation of TSNAs in tobaccos cured in this manner (Boyette and Hamm (2001) *Rec. Adv. Tob, Sci.* 27:17-22.). In contrast, in the air-cured Burley tobaccos, TSNA formation proceeds primarily through reaction of tobacco alkaloids with nitrite, a process catalyzed by leaf-borne microbes (Bush et al. (2001) *Rec. Adv. Tob. Sci,* 27:23-46). Thus far, attempts to reduce TSNAs through modification of curing conditions while maintaining acceptable quality standards have not proven to be successful for the air-cured tobaccos.

SUMMARY OF THE INVENTION

In an aspect, the present invention includes a seed of tobacco cultivar NCBEX1F, a representative sample seed of the cultivar having been deposited with the ATCC under ATCC Accession No. PTA-11718.

In another aspect, the present invention includes a tobacco plant, or part thereof, produced by growing the seed of tobacco cultivar NCBEX1F, a representative sample seed of the cultivar having been deposited with the ATCC under ATCC Accession No. PTA-11718.

In a further aspect, the present invention includes a harvested leaf, or part thereof, of a tobacco plant, or part thereof, produced by growing the seed of tobacco cultivar NCBEX1F, a representative sample seed of the cultivar having been deposited with the ATCC under ATCC Accession No. PTA-11718.

In an aspect, the present invention includes a harvested leaf, or part thereof, of a tobacco plant, produced by growing the seed of tobacco cultivar NCBEX1F, a representative sample seed of the cultivar having been deposited with the ATCC under ATCC Accession No. PTA-11718, where the leaf has a reduced amount of nornicotine and/or N'-nitrosonornicotine (NNN) and/or more stably low nicotine conversion as compared to a leaf from TN 90 LC or most other commercial burley tobacco cultivars grown under similar conditions.

In an aspect, the present invention includes a harvested leaf, or part thereof, produced by growing the seed of tobacco cultivar NCBEX1F, a representative sample seed of the cultivar having been deposited with the ATCC under ATCC Accession No. PTA-11718, where the leaf has a reduced amount of nornicotine and/or N'-nitrosonornicotine (NNN) and/or more stably low nicotine conversion as compared to-a leaf from TN 90 LC or most other commercial burley tobacco cultivars grown under similar conditions, and the reduced amount of nornicotine and/or N'-nitrosonornicotine (NNN) is reduced in a smoke stream produced from burning the leaf as compared to burning a leaf from TN 90 LC or most other commercial burley tobacco cultivars grown under similar conditions.

In a further aspect, the present invention includes a tobacco product, prepared from a tobacco plant, or part thereof, produced by growing the seed of tobacco cultivar NCBEX1F, a representative sample seed of the cultivar having been deposited with the ATCC under ATCC Accession No. PTA-11718, where the product is selected from the group consisting of pipe tobacco, cigar tobacco, cigarette tobacco, chewing tobacco, leaf tobacco, shredded tobacco, and cut tobacco.

In an aspect, the present invention includes a tobacco product, prepared from a tobacco plant, or part thereof, produced by growing the seed of tobacco cultivar NCBEX1F, a representative sample seed of the cultivar having been deposited with the ATCC under ATCC Accession No. PTA-11718, where the product is selected from the group consisting of a cigarillo, a non-ventilated recess filter cigarette, a vented recess filter cigarette, a cigar, snuff, and chewing tobacco.

In another aspect, the present invention includes a tobacco product, prepared from a tobacco plant, or part thereof, produced by growing the seed of tobacco cultivar NCBEX1F, a representative sample seed of the cultivar having been deposited with the ATCC under ATCC Accession No. PTA-11718, where the product is selected from the group consisting of a cigarillo, a non-ventilated recess filter cigarette, a vented recess filter cigarette, a cigar, snuff, and chewing tobacco, and where the product has a reduced amount of nornicotine and/or N'-nitrosonornicotine (NNN) and/or more stably low nicotine conversion as compared to a product prepared from TN 90 LC or most other commercial burley tobacco cultivars grown and processed under similar conditions.

In an aspect, the present invention includes a part of a tobacco plant, produced by growing the seed of tobacco cultivar NCBEX1F, a representative sample seed of the cultivar having been deposited with the ATCC under ATCC Accession No. PTA-11718, where the part is selected from the group consisting of leaf, pollen, ovule, embryo, cotyledon, hypocotyl, meristematic cell, protoplast, root, root tip, pistil, anther, flower, shoot, stem, pod and petiole.

In another aspect, the present invention includes a tissue culture produced from a protoplast or cell from a tobacco plant, or part thereof, produced by growing the seed of tobacco cultivar NCBEX1F, a representative sample seed of the cultivar having been deposited with the ATCC under ATCC Accession No. PTA-11718, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod and petiole.

In an aspect, the present invention includes a tobacco plant regenerated from a tissue culture produced from a protoplast or cell from a tobacco plant, or part thereof, produced by growing the seed of tobacco cultivar NCBEX1F, a representative sample seed of the cultivar having been deposited with the ATCC under ATCC Accession No. PTA-11718, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod and petiole and the regenerated plant has essentially all of the morphological and physiological characteristics of cultivar NCBEX1F when grown under the same environmental conditions.

In another aspect, the present invention includes a seed of tobacco cultivar NC EX90.

In an aspect, the present invention includes a tobacco plant, or part thereof, produced by growing a seed of tobacco cultivar NC EX90.

In a further aspect, the present invention includes a harvested leaf, or part thereof, of a tobacco plant, produced by growing the seed of tobacco cultivar NC EX90.

In another aspect, the present invention includes a harvested leaf, or part thereof, of a tobacco plant, produced by growing the seed of tobacco cultivar NC EX 90, where the leaf has a reduced amount of nornicotine and/or N'-nitrosonornicotine (NNN) and/or more stably low nicotine conversion as compared to a leaf from TN 90 LC or most other commercial burley tobacco cultivars grown under similar conditions.

In an aspect, the present invention includes a harvested leaf, or part thereof, of a tobacco plant, produced by growing the seed of tobacco cultivar NC EX90, where the leaf has a reduced amount of nornicotine and/or N'-nitrosonornicotine (NNN) and/or more stably low nicotine conversion as compared to a leaf from TN 90 LC or most other commercial burley tobacco cultivars grown under similar conditions, and the reduced amount of nornicotine and/or N'-nitrosonornicotine (NNN) is reduced in a smoke stream produced from burning the leaf as compared to burning a leaf from TN 90 LC or most other commercial burley tobacco cultivars when grown under similar conditions.

In a further aspect, the present invention includes a tobacco product, prepared from a tobacco plant, or part thereof, produced by growing the seed of tobacco cultivar NC EX90, where the product is selected from the group consisting of pipe tobacco, cigar tobacco, cigarette tobacco, chewing tobacco, leaf tobacco, shredded tobacco, and cut tobacco.

In an aspect, the present invention includes a tobacco product, prepared from a tobacco plant, or part thereof, produced by growing the seed of tobacco cultivar NC EX90, where the product is selected from the group consisting of a cigarillo, a non-ventilated recess filter cigarette, a vented recess filter cigarette, a cigar, snuff, and chewing tobacco.

In another aspect, the present invention includes a tobacco product, prepared from a tobacco plant, or part thereof, produced by growing the seed of tobacco cultivar NC EX90, where the product is selected from the group consisting of a cigarillo, a non-ventilated recess filter cigarette, a vented recess filter cigarette, a cigar, snuff, and chewing tobacco where the product has a reduced amount of nornicotine and/or N'-nitrosonornicotine (NNN) and/or more stably low nicotine conversion as compared to a product prepared from TN 90 LC or most other commercial burley tobacco cultivars grown and processed under similar conditions.

In an aspect, the present invention includes a part of a tobacco plant, produced by growing a seed of tobacco cultivar NC EX90, where the part is selected from the group consisting of leaf, pollen, ovule, embryo, cotyledon, hypocotyl, meristematic cell, protoplast, root, root tip, pistil, anther, flower, shoot, stem, pod and petiole.

In a further aspect, the present invention includes a tissue culture produced from a protoplast or cell from a tobacco plant, or part thereof, produced by growing the seed of tobacco cultivar NC EX90, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod and petiole.

In an aspect, the present invention includes a tobacco plant regenerated from a tissue culture produced from a protoplast or cell from a tobacco plant, or part thereof, produced by growing the seed of tobacco cultivar NC EX90, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod and petiole, and the regenerated plant has essentially all of the morphological and physiological characteristics of cultivar NC EX90 when grown under the same environmental conditions.

In another aspect, the present invention includes a seed of tobacco cultivar NCBEX1MS, a representative sample seed of the cultivar having been deposited with the ATCC under ATCC Accession No. PTA-11719.

In an aspect, the present invention includes a tobacco plant, or part thereof, produced by growing the seed of tobacco cultivar NCBEX1F, a representative sample seed of the cultivar having been deposited with the ATCC under ATCC Accession No. PTA-11719.

In another aspect, the present invention includes a harvested leaf, or part thereof, of a tobacco plant produced by growing the seed of tobacco cultivar NCBEX1MS, a representative sample seed of the cultivar having been deposited with the ATCC under ATCC Accession No. PTA-11719.

In an aspect, the present invention includes a harvested leaf, or part thereof, of a tobacco plant, produced by growing the seed of tobacco cultivar NCBEX1MS, a representative sample seed of the cultivar having been deposited with the ATCC under ATCC Accession No. PTA-11719, where the leaf has a reduced amount of nornicotine and/or N'-nitrosonornicotine (NNN) and/or more stably low nicotine conversion as compared to a leaf from TN 90 LC or most other commercial burley tobacco cultivars grown under similar conditions.

In another aspect, the present invention includes a harvested leaf, or part thereof, of a tobacco plant, produced by growing the seed of tobacco cultivar NCBEX1MS, a representative sample seed of the cultivar having been deposited with the ATCC under ATCC Accession No. PTA-11719, where the leaf has a reduced amount of nornicotine and/or N'-nitrosonornicotine (NNN) and/or more stably low nicotine conversion as compared to a leaf from TN 90 LC or most other commercial burley tobacco cultivars when grown under similar conditions, and the reduced amount of nornicotine and/or N'-nitrosonornicotine (NNN) is reduced in a smoke stream produced from burning the leaf as compared to burning a leaf from TN 90 LC or most other commercial burley tobacco cultivars grown under similar conditions.

In a further aspect, the present invention includes a tobacco product, prepared from a tobacco plant, or part thereof, produced by growing the seed of tobacco cultivar NCBEX1MS, a representative sample seed of the cultivar having been deposited with the ATCC under ATCC Accession No. PTA-11719, where the product is selected from the group consisting of pipe tobacco, cigar tobacco, cigarette tobacco, chewing tobacco, leaf tobacco, shredded tobacco, and cut tobacco.

In an aspect, the present invention includes a tobacco product, prepared from a tobacco plant, or part thereof, produced by growing the seed of tobacco cultivar NCBEX1MS, a representative sample seed of the cultivar having been deposited with the ATCC under ATCC Accession No. PTA-11719, where the product is selected from the group consisting of a cigarillo, a non-ventilated recess filter cigarette, a vented recess filter cigarette, a cigar, snuff, and chewing tobacco.

In another aspect, the present invention includes a tobacco product, prepared from a tobacco plant, or part thereof, produced by growing the seed of tobacco cultivar NCBEX1MS, a representative sample seed of the cultivar having been deposited with the ATCC under ATCC Accession No. PTA-11719, where the product is selected from the group consisting of a cigarillo, a non-ventilated recess filter cigarette, a vented recess filter cigarette, a cigar, snuff, and chewing tobacco, where the product has a reduced amount of nornicotine and/or N'-nitrosonornicotine (NNN) and/or more stably low nicotine conversion as compared to a product prepared from TN 90 LC or most other commercial burley tobacco cultivars grown and processed under similar conditions.

In an aspect, the present invention includes a part of a tobacco plant, produced by growing the seed of tobacco cultivar NCBEX1MS, a representative sample seed of the cultivar having been deposited with the ATCC under ATCC Accession No. PTA-11719, where the part is selected from the group consisting of leaf, pollen, ovule, embryo, cotyledon, hypocotyl, meristematic cell, protoplast, root, root tip, pistil, anther, flower, shoot, stem, pod and petiole.

In another aspect, the present invention includes a tissue culture produced from a protoplast or cell from a tobacco plant, or part thereof, produced by growing the seed of tobacco cultivar NCBEX1MS, a representative sample seed of the cultivar having been deposited with the ATCC under ATCC Accession No. PTA-11719, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod and petiole.

In an aspect, the present invention includes a tobacco plant regenerated from a tissue culture produced from a protoplast or cell from a tobacco plant, or part thereof, produced by growing the seed of tobacco cultivar NCBEX1MS, a representative sample seed of the cultivar having been deposited with the ATCC under ATCC Accession No. PTA-11719, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod and petiole, and the plant has essentially all of the morphological and physiological characteristics of cultivar NCBEX1MS when grown under the same environmental conditions.

In an aspect, the present invention includes an $F_1$ progeny plant of tobacco cultivar NCBEX1F, a representative sample seed of the cultivar having been deposited with the ATCC under ATCC Accession No. PTA-11718.

In an aspect, the present invention includes an $F_1$ progeny plant of tobacco cultivar NCBEX1MS, a representative sample seed of the cultivar having been deposited with the ATCC under ATCC Accession No. PTA-11719.

In an aspect, the present invention includes an $F_1$ progeny plant of tobacco cultivar NC EX90.

In another aspect, the present invention includes an $F_1$ progeny plant of tobacco cultivar NCBEX1F, a representative sample seed of the cultivar having been deposited with the ATCC under ATCC Accession No. PTA-11718, where the $F_1$ plant is cytoplasmic male sterile (CMS).

In another aspect, the present invention includes a method for producing a tobacco seed comprising crossing two tobacco plants and harvesting the resultant tobacco seed, where at least one tobacco plant is a tobacco plant produced by growing the seed of tobacco cultivar NCBEX1F, a representative sample seed of the cultivar having been deposited with the ATCC under ATCC Accession No. PTA-11718.

In another aspect, the present invention includes a method for producing a tobacco seed comprising crossing two tobacco plants and harvesting the resultant tobacco seed, where at least one tobacco plant is a tobacco plant produced by growing the seed of tobacco cultivar NCBEX1F, a representative sample seed of the cultivar having been deposited with the ATCC under ATCC Accession No. PTA-11718, where the plant of tobacco cultivar NCBEX1F is the female parent.

In another aspect, the present invention includes a method for producing a tobacco seed comprising crossing two tobacco plants and harvesting the resultant tobacco seed, where at least one tobacco plant is a tobacco plant produced by growing the seed of tobacco cultivar NCBEX1F, a representative sample seed of the cultivar having been deposited with the ATCC under ATCC Accession No. PTA-11718, where at least one tobacco plant is cytoplasmic male sterile (CMS).

In another aspect, the present invention includes an $F_1$ progeny seed produced by a method comprising crossing two tobacco plants and harvesting the resultant tobacco seed, where at least one tobacco plant is a tobacco plant produced by growing the seed of tobacco cultivar NCBEX1F, a representative sample seed of the cultivar having been deposited with the ATCC under ATCC Accession No. PTA-11718, where at least one tobacco plant is cytoplasmic male sterile (CMS).

In an aspect, the present invention also includes a container of $F_1$ progeny seeds produced by a method comprising crossing two tobacco plants and harvesting the resultant tobacco seed, where at least one tobacco plant is a tobacco plant produced by growing the seed of tobacco cultivar NCBEX1F, a representative sample seed of the cultivar having been deposited with the ATCC under ATCC Accession No. PTA-11718, where at least one tobacco plant is cytoplasmic male sterile (CMS).

In an aspect, the present invention includes an $F_t$ progeny plant produced by growing a seed produced by a method comprising crossing two tobacco plants and harvesting the resultant tobacco seed, where at least one tobacco plant is a tobacco plant produced by growing the seed of tobacco cultivar NCBEX1F, a representative sample seed of the cultivar having been deposited with the ATCC under ATCC Accession No. PTA-11718, and where at least one tobacco plant is cytoplasmic male sterile (CMS).

In an aspect, the present invention also includes a harvested leaf of an $F_1$ progeny plant produced by growing a seed produced by a method comprising crossing two tobacco plants and harvesting the resultant tobacco seed, where at least one tobacco plant is a tobacco plant produced by growing the seed of tobacco cultivar NCBEX1F, a representative sample seed of the cultivar having been deposited with the ATCC under ATCC Accession No. PTA-11718, and where at least one tobacco plant is cytoplasmic male sterile (CMS).

In another aspect, the present invention further includes a harvested leaf of an $F_1$ progeny plant having a reduced amount of nornicotine and/or N'-nitrosonornicotine (NNN) and/or more stably low nicotine conversion as compared to a leaf from TN 90 LC or most other commercial burley tobacco cultivars grown under similar conditions, produced by growing a seed produced by a method comprising crossing two tobacco plants and harvesting the resultant tobacco seed, where at least one tobacco plant is a tobacco plant produced by growing the seed of tobacco cultivar NCBEX1F, a representative sample seed of the cultivar having been deposited with the ATCC under ATCC Accession No. PTA-11718, and where at least one tobacco plant is cytoplasmic male sterile (CMS).

In an aspect, the present invention also includes a harvested leaf of an $F_1$ progeny plant, wherein the harvested leaf has a reduced amount of nornicotine and/or N'-nitrosonornicotine (NNN) in a smoke stream produced from burning the leaf as compared to burning a leaf from TN 90 LC or most other commercial burley tobacco cultivars grown under similar conditions, where the plant is produced by growing a seed produced by a method comprising crossing two tobacco plants and harvesting the resultant tobacco seed, where at least one tobacco plant is a tobacco plant produced by growing the seed of tobacco cultivar NCBEX1F, a representative sample seed of the cultivar having been deposited with the ATCC under ATCC Accession No. PTA-11718, and where at least one tobacco plant is cytoplasmic male sterile (CMS).

In an aspect, the present invention includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar NCBEX1F, a representative sample seed of the cultivar having been deposited with the ATCC under ATCC Accession No. PTA-11718, where at least one tobacco plant is cytoplasmic male sterile, and where the tobacco product is selected from the group consisting of pipe tobacco, cigar tobacco, cigarette tobacco, chewing tobacco, leaf tobacco, shredded tobacco, and cut tobacco.

In an aspect, the present invention further includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar NCBEX1F, a representative sample seed of the cultivar having been deposited with the ATCC under ATCC Accession No. PTA-11718, where at least one tobacco plant is cytoplasmic male sterile, and where the tobacco product is selected from the group consisting of a cigarillo, a non-ventilated recess filter cigarette, a vented recess filter cigarette, a cigar, snuff, and chewing tobacco.

In an aspect, the present invention further includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar NCBEX1F, a representative sample seed of the cultivar having been deposited with the ATCC under ATCC Accession No. PTA-11718, where at least one tobacco plant is cytoplasmic male sterile, and where the tobacco product is selected from the group consisting of a cigarillo, a non-ventilated recess filter cigarette, a vented recess filter cigarette, a cigar, snuff, and chewing tobacco, and further where the product has a reduced amount of nornicotine and/or N'-nitrosonornicotine (NNN) and/or more stably low nicotine conversion as compared to a product prepared from TN 90 LC or most other commercial burley tobacco cultivars grown and processed under similar conditions.

In an aspect, the present invention includes a progeny plant of tobacco cultivar NCBEX1F, a representative sample seed of the cultivar having been deposited with the ATCC under ATCC Accession No. PTA-11718.

In an aspect, the present invention includes a progeny plant of tobacco cultivar NCBEX1MS, a representative sample seed of the cultivar having been deposited with the ATCC under ATCC Accession No. PTA-11719.

In an aspect, the present invention includes a progeny plant of tobacco cultivar NC EX90.

In another aspect, the present invention includes a progeny plant of tobacco cultivar NCBEX1F, a representative sample seed of the cultivar having been deposited with the ATCC under ATCC Accession No. PTA-11718, where the progeny plant is cytoplasmic male sterile (CMS).

In another aspect, the present invention includes a method for producing a tobacco seed comprising crossing two tobacco plants and harvesting the resultant tobacco seed, where at least one tobacco plant is a tobacco plant produced by growing the seed of tobacco cultivar NCBEX1F, a representative sample seed of the cultivar having been deposited with the ATCC under ATCC Accession No. PTA-11718.

In another aspect, the present invention includes a method for producing a tobacco seed comprising crossing two tobacco plants and harvesting the resultant tobacco seed, where at least one tobacco plant is a tobacco plant produced by growing the seed of tobacco cultivar NCBEX1F, a representative sample seed of the cultivar having been deposited with the ATCC under ATCC Accession No. PTA-11718, where the plant of tobacco cultivar NCBEX1F is the female parent.

In another aspect, the present invention includes a method for producing a tobacco seed comprising crossing two tobacco plants and harvesting the resultant tobacco seed, where at least one tobacco plant is a tobacco plant produced by growing the seed of tobacco cultivar NCBEX1F, a representative sample seed of the cultivar having been deposited with the ATCC under ATCC Accession No. PTA-11718, where at least one tobacco plant is cytoplasmic male sterile (CMS).

In another aspect, the present invention includes a progeny seed produced by a method of comprising crossing two tobacco plants and harvesting the resultant tobacco seed, where at least one tobacco plant is a tobacco plant produced by growing the seed of tobacco cultivar NCBEX1F, a representative sample seed of the cultivar having been deposited with the ATCC under ATCC Accession No. PTA-11718, where at least one tobacco plant is cytoplasmic male sterile (CMS).

In an aspect, the present invention also includes a container of progeny seeds produced by a method comprising crossing two tobacco plants and harvesting the resultant tobacco seed, where at least one tobacco plant is a tobacco plant produced by growing the seed of tobacco cultivar NCBEX1F, a representative sample seed of the cultivar having been deposited with the ATCC under ATCC Accession No. PTA-11718, where at least one tobacco plant is cytoplasmic male sterile (CMS).

In an aspect, the present invention includes a progeny plant produced by growing a seed produced by a method comprising crossing two tobacco plants and harvesting the resultant tobacco seed, where at least one tobacco plant is a tobacco plant produced by growing the seed of tobacco cultivar NCBEX1F, a representative sample seed of the cultivar having been deposited with the ATCC under ATCC Accession No. PTA-11718, and where at least one tobacco plant is cytoplasmic male sterile (CMS).

In an aspect, the present invention also includes a harvested leaf of a progeny plant produced by growing a seed produced by a method comprising crossing two tobacco plants and harvesting the resultant tobacco seed, where at least one tobacco plant is a tobacco plant produced by growing the seed of tobacco cultivar NCBEX1F, a representative sample seed of the cultivar having been deposited with the ATCC under ATCC Accession No. PTA-11718, and where at least one tobacco plant is cytoplasmic male sterile (CMS).

In another aspect, the present invention further includes a harvested leaf of a progeny plant having a reduced amount of nornicotine and/or N'-nitrosonornicotine (NNN) and/or more stably low nicotine conversion as compared to a leaf from TN 90 LC or most other commercial burley tobacco cultivars grown under similar conditions, produced by growing a seed produced by a method comprising crossing two tobacco plants and harvesting the resultant tobacco seed, where at least one tobacco plant is a tobacco plant produced by growing the seed of tobacco cultivar NCBEX1F, a representative sample seed of the cultivar having been deposited with the ATCC under ATCC Accession No. PTA-11718, and where at least one tobacco plant is cytoplasmic male sterile (CMS).

In an aspect, the present invention also includes a harvested leaf of a progeny plant, wherein the harvested leaf has a reduced amount of nornicotine and/or N'-nitrosonornicotine (NNN) in a smoke stream produced from burning the leaf as compared to burning a leaf from TN 90 LC or most other commercial burley tobacco cultivars grown under similar conditions, where the plant is produced by growing a seed produced by a method comprising crossing two tobacco plants and harvesting the resultant tobacco seed, where at least one tobacco plant is a tobacco plant produced by growing the seed of tobacco cultivar NCBEX1F, a representative sample seed of the cultivar having been deposited with the ATCC under ATCC Accession No. PTA-11718, and where at least one tobacco plant is cytoplasmic male sterile (CMS).

In an aspect, the present invention includes a tobacco product prepared from a progeny tobacco plant, or part thereof, where the plant or part thereof is produced by growing a progeny seed produced by a method comprising crossing two tobacco plants and harvesting the resultant tobacco seed, where at least one tobacco plant is produced by growing a seed of tobacco cultivar NCBEX1F, a representative sample seed of the cultivar having been deposited with the ATCC under ATCC Accession No. PTA-11718, where at least one tobacco plant is cytoplasmic male sterile, and where the tobacco product is selected from the group consisting of pipe tobacco, cigar tobacco, cigarette tobacco, chewing tobacco, leaf tobacco, shredded tobacco, and cut tobacco.

In an aspect, the present invention further includes a tobacco product prepared from a progeny tobacco plant, or part thereof, where the plant or part thereof is produced by growing a progeny seed produced by a method comprising crossing two tobacco plants and harvesting the resultant tobacco seed, where at least one tobacco plant is produced by growing a seed of tobacco cultivar NCBEX1F, a representative sample seed of the cultivar having been deposited with the ATCC under ATCC Accession No. PTA-11718, where at least one tobacco plant is cytoplasmic male sterile, and where the tobacco product is selected from the group consisting of a cigarillo, a non-ventilated recess filter cigarette, a vented recess filter cigarette, a cigar, snuff, and chewing tobacco.

In an aspect, the present invention further includes a tobacco product prepared from a progeny tobacco plant, or part thereof, where the plant or part thereof is produced by growing a progeny seed produced by a method comprising crossing two tobacco plants and harvesting the resultant tobacco seed, where at least one tobacco plant is produced by growing a seed of tobacco cultivar NCBEX1F, a representative sample seed of the cultivar having been deposited with the ATCC under ATCC Accession No. PTA-11718, where at least one tobacco plant is cytoplasmic male sterile, and where the tobacco product is selected from the group consisting of a cigarillo, a non-ventilated recess filter cigarette, a vented recess filter cigarette, a cigar, snuff, and chewing tobacco, and further where the product has a reduced amount of nornicotine and/or N'-nitrosonornicotine (NNN) and/or more stably low nicotine conversion as compared to a product prepared from TN 90 LC or most other commercial burley tobacco cultivars grown and processed under similar conditions.

In an aspect, the present invention includes a method for producing a tobacco seed comprising crossing two tobacco plants and harvesting the resultant tobacco seed, where at least one tobacco plant is cytoplasmic male sterile, where the cytoplasmic male sterile plant is a plant of tobacco cultivar NCBEX1MS, a representative sample seed of the cultivar having been deposited with the ATCC under ATCC Accession No. PTA-11719.

In an aspect, the present invention includes a method of vegetatively propagating a plant of a tobacco cultivar comprising the steps of (a) culturing tissue capable of being propagated from a plant of a tobacco cultivar selected from the group consisting of NCBEX1F, a representative sample seed of the cultivar having been deposited with the ATCC under ATCC Accession No. PTA-11718, NCBEX1MS, a representative sample seed of the cultivar having been deposited with the ATCC under ATCC Accession No. PTA-11719, and NC EX90 to obtain a proliferated shoot; and (b) rooting the proliferated shoots to obtain a rooted plantlet.

In an aspect, the present invention includes a method of vegetatively propagating a plant of a tobacco cultivar comprising the steps of (a) culturing tissue capable of being propagated from a plant of a tobacco cultivar selected from the group consisting of NCBEX1F, a representative sample seed of the cultivar having been deposited with the ATCC under ATCC Accession No. PTA-11718, NCBEX1MS, a representative sample seed of the cultivar having been deposited with the ATCC under ATCC Accession No. PTA-11719, and NC EX90 to obtain a proliferated shoot; (b) rooting the proliferated shoots to obtain a rooted plantlet; and (c) growing a plant from the rooted plantlet.

In an aspect, the present invention includes a method of introducing a desired trait into a tobacco cultivar comprising: (a) crossing a plant of a tobacco cultivar selected from the group consisting of NCBEX1F, a representative sample seed of the cultivar having been deposited with the ATCC under ATCC Accession No. PTA-11718, NCBEX1MS, a representative sample seed of the cultivar having been deposited with the ATCC under ATCC Accession No. PTA-11719, and NC EX90, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of a tobacco cultivar selected from the group consisting of NCBEX1F, NCBEX1MS, and NC EX90 to produce a backcross $F_2$ progeny seed; (d) growing the $F_2$ progeny seed and selecting a backcross $F_2$ progeny plant comprising the desired trait; and (e) repeating steps (c) and (d) three or more times in succession to produce selected fourth or higher backcross progeny that comprise the desired trait and essentially all of the physiological and morphological characteristics of a tobacco cultivar selected from the group consisting of NCBEX1F, NCBEX1MS, and NC EX90, when grown under the same environmental conditions.

In an aspect, the present invention includes a method of introducing a desired trait into a tobacco cultivar comprising: (a) crossing a plant of a tobacco cultivar selected from the group consisting of NCBEX1F, a representative sample seed of the cultivar having been deposited with the ATCC under ATCC Accession No. PTA-11718, NCBEX1MS, a representative sample seed of the cultivar having been deposited with the ATCC under ATCC Accession No. PTA-11719, and NC EX90, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of a tobacco cultivar selected from the group consisting of NCBEX1F, NCBEX1MS, and NC EX90 to produce a backcross $F_2$ progeny seed; (d) growing the $F_2$ progeny seed and selecting a backcross $F_2$ progeny plant comprising the desired trait; and (e) repeating steps (c) and (d) three or more times in succession to produce selected fourth or higher backcross progeny that comprise the desired trait and essentially all of the physiological and morphological characteristics of a tobacco cultivar selected from the group consisting of NCBEX1F, NCBEX1MS, and NC EX90 when grown under the same environmental conditions, where the trait is cytoplasmic male sterility (CMS).

In an aspect, the present invention includes a method of introducing a desired trait into a tobacco cultivar comprising: (a) crossing a plant of a tobacco cultivar selected from the group consisting of NCBEX1F, a representative sample seed of the cultivar having been deposited with the ATCC under ATCC Accession No. PTA-11718, NCBEX1MS, a representative sample seed of the cultivar having been deposited with the ATCC under ATCC Accession No. PTA-11719, and NC EX90, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of a tobacco cultivar selected from the group consisting of NCBEX1F, NCBEX1MS, and NC EX90 to produce a backcross $F_2$ progeny seed; (d) growing the $F_2$ progeny seed and selecting a backcross $F_2$ progeny plant comprising the desired trait; and (e) repeating steps (c) and (d) three or more times in succession to produce selected fourth or higher backcross progeny that comprise essentially all of the physiological and morphological characteristics of a tobacco cultivar selected from the group consisting of NCBEX1F, NCBEX1MS, and NC EX90 when grown under the same environmental conditions, and the desired trait, where the trait is cytoplasmic male sterility (CMS) and the CMS trait is obtained from the cytoplasm of *Nicotiana suaveolens*.

In an aspect, the present invention includes a method of introducing a desired trait into a tobacco cultivar comprising: (a) crossing a plant of a tobacco cultivar selected from the group consisting of NCBEX1F, a representative sample seed of the cultivar having been deposited with the ATCC under ATCC Accession No. PTA-11718, NCBEX1MS, a representative sample seed of the cultivar having been deposited with the ATCC under ATCC Accession No. PTA-11719, and NC EX90, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of a tobacco cultivar selected from the group consisting of NCBEX1F, NCBEX1MS, and NC EX90 to produce a backcross $F_2$ progeny seed; (d) growing the $F_2$ progeny seed and selecting a backcross $F_2$ progeny plant comprising the desired trait; and (e) repeating steps (c) and (d) three or more times in succession to produce selected fourth or higher backcross progeny that comprise essentially all of the physiological and morphological characteristics of a tobacco cultivar selected from the group consisting of NCBEX1F, NCBEX1MS, and NC EX90 when grown under the same environmental conditions, and the desired trait, where the trait is cytoplasmic male sterility (CMS) and the CMS trait is obtained from the cytoplasm of *Nicotiana suaveolens*, and where the second tobacco plant is TN 90 LC CMS.

In an aspect, the present invention includes a tobacco plant produced by a method comprising introducing a desired trait into a tobacco cultivar comprising: (a) crossing a plant of a tobacco cultivar selected from the group consisting of NCBEX1F, a representative sample seed of the cultivar having been deposited with the ATCC under ATCC Accession No. PTA-11718, NCBEX1MS, a representative sample seed of the cultivar having been deposited with the ATCC under ATCC Accession No. PTA-11719, and NC EX90, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of a tobacco cultivar selected from the group consisting of NCBEX1F, NCBEX1MS, and NC EX90 to produce a backcross $F_2$ progeny seed; (d) growing the $F_2$ progeny seed and selecting a backcross $F_2$ progeny plant comprising the desired trait; and (e) repeating steps (c) and (d) three or more times in succession to produce selected fourth or higher backcross progeny that comprise the desired trait and essentially all of the physiological and morphological characteristics of a tobacco cultivar selected from the group consisting of NCBEX1F, NCBEX1MS, and NC EX90, when grown under the same environmental conditions.

In another aspect, the present invention includes a method of introducing a desired trait into a tobacco cultivar comprising: (a) crossing a plant of a tobacco cultivar selected from the group consisting of NCBEX1F, a representative sample seed of the cultivar having been deposited with the ATCC under ATCC Accession No. PTA-11718, NCBEX1MS, a representative sample seed of the cultivar having been deposited with the ATCC under ATCC Accession No. PTA-11719, and NC EX90, with a plant of another tobacco cultivar that comprises a desired trait to produce a progeny plant where the desired trait is selected from the group consisting of herbicide resistance, pest resistance, disease resistance, high yield, high grade index, curability, curing quality, mechanical harvestability, holding ability, leaf quality, height, plant maturation, early maturing, early to medium maturing, medium maturing, medium to late maturing, late maturing; small stalk, medium stalk, large stalk, leaf number per plant, 5-10 leaves per plant, 11-15 leaves per plant, 16-21 leaves per plant, and any combination thereof, to produce an $F_1$ progeny seed; (b) growing the $F_1$ progeny seed into an $F_1$ progeny plant and selecting the $F_1$ progeny plant having the desired trait; (c) crossing the selected $F_1$ progeny plant with a plant of a tobacco cultivar selected from the group consisting of NCBEX1F, NCBEX1MS, and NC EX90 to produce a backcross F2 progeny plant seed; (d) growing the backcross F2 progeny plant seed into a backcross F2 progeny plant and selecting a F2 backcross progeny plant comprising the desired trait; and (e) repeating steps (c) and (d) one or more times in succession to produce a selected fourth or higher backcross progeny plant that comprises the desired trait and essentially all of the physiological and morphological characteristics of a tobacco cultivar selected from the group consisting of NCBEX1F, NCBEX1MS, and NC EX90, when grown under the same environmental conditions.

In another aspect, the present invention includes a method of introducing a desired trait into a tobacco cultivar comprising: (a) crossing a plant of a tobacco cultivar selected from the group consisting of NCBEX1F, a representative sample seed of the cultivar having been deposited with the ATCC under ATCC Accession No. PTA-11718, NCBEX1MS, a representative sample seed of the cultivar having been deposited with the ATCC under ATCC Accession No. PTA-11719, and NC EX90, with a plant of another tobacco cultivar that comprises a desired trait to produce a progeny plant where the desired trait is selected from the group consisting of herbicide resistance, pest resistance, disease resistance, high yield, high grade index, curability, curing quality, mechanical harvestability, holding ability, leaf quality, height, plant maturation, early maturing, early to medium maturing, medium maturing, medium to late maturing, late maturing; small stalk, medium stalk, large stalk, leaf number per plant, 5-10 leaves per plant, 11-15 leaves per plant, 16-21 leaves per plant, and any combination thereof, to produce an $F_1$ progeny seed; (b) growing the $F_1$ progeny seed into an $F_1$ progeny plant and selecting the $F_1$ progeny plant having the desired trait; (c) crossing the selected $F_1$ progeny plant with a plant of a tobacco cultivar selected from the group consisting of NCBEX1F, NCBEX1MS, and NC EX90 to produce a backcross progeny plant seed; (d) growing the backcross progeny plant seed into a backcross progeny plant and selecting the backcross progeny plant comprising the desired trait; and (e) repeating steps (c) and (d) one or more times in succession to produce a selected fourth or higher backcross progeny plant that comprises the desired trait and essentially all of the physiological and morphological characteristics of a tobacco cultivar selected from the group consisting of NCBEX1F, NCBEX1MS, and NC EX90 when grown under the same environmental conditions.

In another aspect, the present invention includes a method of introducing a desired trait into a tobacco cultivar comprising: (a) crossing a plant of a tobacco cultivar selected from the group consisting of NCBEX1F, a representative sample seed of the cultivar having been deposited with the ATCC under ATCC Accession No. PTA-11718, NCBEX1MS, a representative sample seed of the cultivar having been deposited with the ATCC under ATCC Accession No. PTA-11719, and NC EX90, with a plant of another tobacco cultivar that comprises a desired trait to produce a progeny plant where the desired trait is selected from the group consisting of herbicide resistance, pest resistance, disease resistance, high yield, high grade index, curability, curing quality, mechanical harvestability, holding ability, leaf quality, height, plant maturation, early maturing, early to medium maturing, medium maturing, medium to late maturing, late maturing; small stalk, medium stalk, large stalk, leaf number per plant, 5-10 leaves per plant, 11-15 leaves per plant, 16-21 leaves per plant, and any combination thereof, to produce an $F_1$ progeny seed; (b) growing the $F_1$ progeny seed into an $F_1$ progeny plant and selecting the $F_1$ progeny plant having the desired trait; (c) crossing the selected $F_1$ progeny plant with a plant of a tobacco cultivar selected from the group consisting of NCBEX1F, NCBEX1MS, and NC EX90 to produce a backcross progeny plant seed; (d) growing the backcross progeny plant seed into a backcross progeny plant and selecting the backcross progeny plant comprising the desired trait and essentially all of the physiological and morphological characteristics of a tobacco cultivar selected from the group consisting of NCBEX1F, NCBEX1MS, and NC EX90, when grown under the same environmental conditions; and (e) repeating steps (c) and (d) one or more times in succession to produce a selected fourth or higher backcross progeny plant that comprises the desired trait and essentially all of the physiological and morphological characteristics of a tobacco cultivar selected from the group consisting of NCBEX1F, NCBEX1MS, and NC EX90, when grown under the same environmental conditions, where the plant has the desired trait of disease resistance.

In another aspect, the present invention includes a method for producing a tobacco plant having decreased and more stable nicotine conversion as compared to TN 90 LC or most other commercial burley tobacco cultivars grown and processed under similar conditions comprising: identifying a first tobacco plant having the nucleotide sequence set forth in SEQ ID NO: 1 or SEQ ID NO: 2; crossing the first tobacco plant with a second tobacco plant and collecting an $F_1$ seed; selfing a plant grown from the $F_1$ seed or crossing a plant grown from the $F_1$ seed to a third tobacco plant to obtain a $F_2$ seed; and identifying a tobacco plant grown from the $F_2$ seed that is homozygous for the nucleotide sequence set forth in SEQ ID NO: 1 or SEQ ID NO: 2.

In an aspect, the present invention includes a method for producing a tobacco plant having decreased and more stable nicotine conversion as compared to TN 90 LC or most other commercial burley tobacco cultivars grown and processed under similar conditions comprising: identifying a first tobacco plant having the nucleotide sequence set forth in SEQ ID NO: 1 or SEQ ID NO: 2; crossing the first tobacco plant with a second tobacco plant and collecting an $F_1$ seed; selfing a plant grown from the $F_1$ seed or crossing a plant grown from the $F_1$ seed to a third tobacco plant to obtain a $F_2$ seed; and identifying a tobacco plant grown from the $F_2$ seed that is homozygous for the nucleotide sequence set forth in SEQ ID NO: 1 or SEQ ID NO: 2, where the second tobacco plant has the nucleotide sequence set forth in SEQ ID NO: 1 or SEQ ID NO: 2.

In an aspect, the present invention includes a method for producing a tobacco plant having decreased and more stable nicotine conversion as compared to TN 90 LC or most other commercial burley tobacco cultivars grown and processed under similar conditions comprising: identifying a first tobacco plant having the nucleotide sequence set forth in SEQ ID NO: 1 or SEQ ID NO: 2; crossing the first tobacco plant with a second tobacco plant and collecting an $F_1$ seed; selfing a plant grown from the $F_1$ seed or crossing a plant grown from the $F_1$ seed to a third tobacco plant to obtain a $F_2$ seed; and identifying a tobacco plant grown from the $F_2$ seed that is homozygous for the nucleotide sequence set forth in SEQ ID NO: 1 or SEQ ID NO: 2, where the second tobacco plant does not have the nucleotide sequence set forth in SEQ ID NO: 1 or SEQ ID NO: 2 and the third tobacco plant is a tobacco plant having the nucleotide sequence set forth in SEQ ID NO: 1 or SEQ ID NO: 2.

In an aspect, the present invention includes for producing a tobacco plant having decreased and more stable nicotine conversion as compared to TN 90 LC or most other commercial burley tobacco cultivars grown and processed under similar conditions comprising: identifying a first tobacco plant having the nucleotide sequence set forth in SEQ ID NO: 1 or SEQ ID NO: 2; crossing the first tobacco plant with a second tobacco plant and collecting an $F_1$ seed; selfing a plant grown from the $F_1$ seed or crossing a plant grown from the $F_1$ seed to a third tobacco plant to obtain a $F_2$ seed; and identifying a tobacco plant grown from the $F_2$ seed that is homozygous for the nucleotide sequence set forth in SEQ ID NO: 1 or SEQ ID NO: 2, where the third tobacco plant is a tobacco plant having the nucleotide sequence set forth in SEQ ID NO: 1 and SEQ ID NO: 2.

In an aspect, the present invention includes a method for producing a tobacco plant having decreased and more stable nicotine conversion as compared to TN 90 LC or most other commercial burley tobacco cultivars grown and processed under similar conditions comprising: identifying a first tobacco plant having the nucleotide sequence set forth in SEQ ID NO: 1 or SEQ ID NO: 2; crossing the first tobacco plant with a second tobacco plant and collecting an $F_1$ seed; selfing a plant grown from the $F_1$ seed or crossing a plant grown from the $F_1$ seed to a third tobacco plant to obtain a $F_2$ seed; and identifying a tobacco plant grown from the $F_2$ seed that is homozygous for the nucleotide sequence set forth in SEQ ID NO: 1 or SEQ ID NO: 2, where the first tobacco plant is a plant of a tobacco cultivar selected from the group consisting of NCBEX1F, a representative sample seed of the cultivar having been deposited with the ATCC under ATCC Accession No. PTA-11718, NCBEX1MS, a representative sample seed of the cultivar having been deposited with the ATCC under ATCC Accession No. PTA-11719, and NC EX90.

In an aspect, the present invention includes a method for producing a tobacco plant having decreased and more stable nicotine conversion as compared to TN 90 LC or most other commercial burley tobacco cultivars grown and processed under similar conditions comprising: identifying a first tobacco plant having the nucleotide sequence set forth in SEQ ID NO: 1 or SEQ ID NO: 2; crossing the first tobacco plant with a second tobacco plant and collecting an $F_1$ seed; selfing a plant grown from the $F_1$ seed or crossing a plant grown from the $F_1$ seed to a third tobacco plant to obtain a $F_2$ seed; and identifying a tobacco plant grown from the $F_2$ seed that is homozygous for the nucleotide sequence set forth in SEQ ID NO: 1 or SEQ ID NO: 2, where the third tobacco plant is a plant of a tobacco cultivar selected from the group consisting of NCBEX1F, a representative sample seed of the cultivar having been deposited with the ATCC under ATCC Accession No. PTA-11718, NCBEX1MS, a representative sample seed of the cultivar having been deposited with the ATCC under ATCC Accession No. PTA-11719, and NC EX90.

In another aspect, the present invention includes a method of producing a plant of a tobacco cultivar selected from the group consisting of NCBEX1F, NCBEX1MS, and NC EX90 having an additional desired trait comprising the steps of: (a) introducing a transgene conferring a desired trait into tissue capable of being propagated from a plant of a tobacco cultivar selected from the group consisting of NCBEX1F, a representative sample seed of the cultivar having been deposited with the ATCC under ATCC Accession No. PTA-11718, NCBEX1MS, a representative sample seed of the cultivar having been deposited with the ATCC under ATCC Accession No. PTA-11719, and NC EX90.

In another aspect, the present invention includes a method of producing an herbicide resistant tobacco plant comprising transforming a tobacco plant, or part thereof, produced by growing a seed of tobacco cultivar NCBEX1F, a representative sample seed of the cultivar having been deposited with the ATCC under ATCC Accession No. PTA-11718, with a transgene where the transgene confers resistance to an herbicide. In some non-limiting examples, the herbicide is selected from the group consisting of imidazolinone, cyclohexanedione, sulfonylurea, glyphosate, glufosinate, phenoxy proprionic acid, L-phosphinothricin, triazine and benzonitrile.

In another aspect, the present invention includes an herbicide resistant tobacco plant produced by a method comprising transforming a tobacco plant, or part thereof, produced by growing a seed of tobacco cultivar NCBEX1F, a representative sample seed of the cultivar having been deposited with the ATCC under ATCC Accession No. PTA-11718, with a transgene where the transgene confers resistance to an herbicide selected from the group consisting of imidazolinone, cyclohexanedione, sulfonylurea, glyphosate, glufosinate, phenoxy proprionic acid, L-phosphinothricin, triazine and benzonitrile.

In another aspect, the present invention includes a method of producing a pest or insect resistant tobacco plant where the method comprises transforming a tobacco plant produced by growing a seed of tobacco cultivar NCBEX1F, a representative sample seed of the cultivar having been deposited with the ATCC under ATCC Accession No. PTA-11718, with a transgene that confers pest or insect resistance.

In a further aspect, the present invention includes a pest or insect resistant tobacco plant produced by a method comprising transforming a tobacco plant produced by growing a seed of tobacco cultivar NCBEX1F, a representative sample seed of the cultivar having been deposited with the ATCC under ATCC Accession No. PTA-11718, with a transgene that confers pest or insect resistance.

In a further aspect, the present invention includes a pest or insect resistant tobacco plant produced by a method comprising transforming a tobacco plant produced by growing a seed of tobacco cultivar NCBEX1F, a representative sample seed of the cultivar having been deposited with the ATCC under ATCC Accession No. PTA-11718, with a transgene that confers pest or insect resistance. In some aspects, the transgene encodes a *Bacillus thuringiensis* (BT) endotoxin.

In another aspect, the present invention includes a method of producing a disease resistant tobacco plant where the method comprises transforming a tobacco plant produced by growing a seed of tobacco cultivar NCBEX1F, a representative sample seed of the cultivar having been deposited with the ATCC under ATCC Accession No. PTA-11718, with a transgene that confers disease resistance.

In a further aspect, the present invention includes a disease resistant tobacco plant produced by a method comprising transforming a tobacco plant produced by growing a seed of tobacco cultivar NCBEX1F, a representative sample seed of the cultivar having been deposited with the ATCC under ATCC Accession No. PTA-11718, with a transgene that confers disease resistance.

BRIEF DESCRIPTION OF THE SEQUENCES

SEQ ID NO: 1 sets forth a cyp82e4 W329Stop nucleotide sequence.

SEQ ID NO: 2 sets forth a cyp82e5v2 W422Stop nucleotide sequence.

SEQ ID NO: 3 sets forth a cyp82e4 W329Stop amino acid sequence.

SEQ ID NO: 4 sets forth a cyp82e5v2 W422Stop amino acid sequence.

SEQ ID NO: 5 sets forth a CYP82E4 wild-type nucleotide sequence.

SEQ ID NO: 6 sets forth a CYP82E5v2 wild-type nucleotide sequence.

SEQ ID NO: 7 sets forth a CYP82E4 wild-type amino acid sequence.

SEQ ID NO: 8 sets forth a CYP82E5v2 wild-type amino acid sequence.

DETAILED DESCRIPTION OF THE INVENTION

Figure 1:
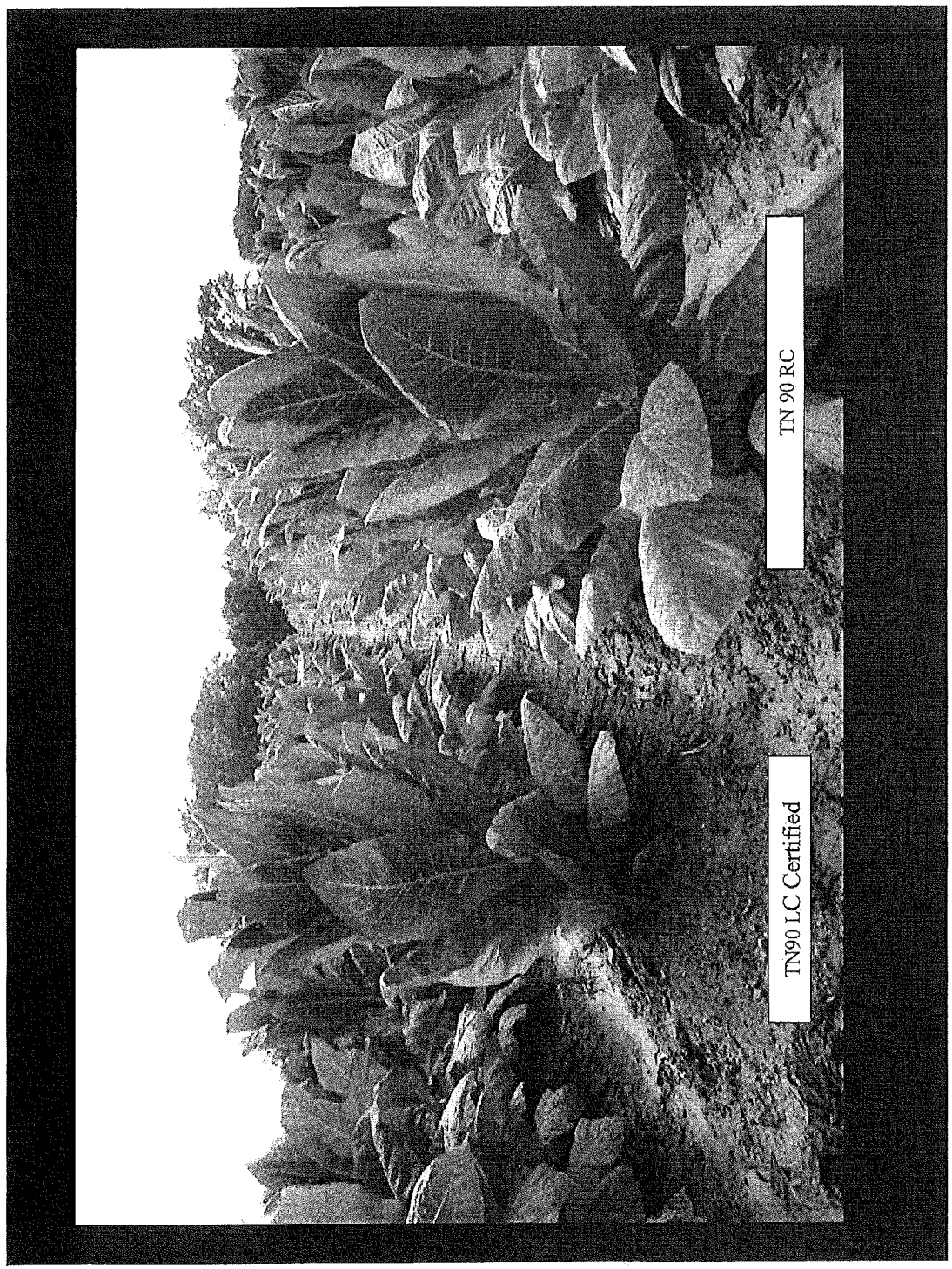
FIG. 1 depicts TN 90 LC certified plants and NC EX90 ("TN 90 RC") plants.

The present invention will now be described more fully hereinafter with reference to the accompanying drawings and specification, in which preferred embodiments of the invention are shown. This invention may, however, be embodied in different forms and should not be construed as limited to the embodiments set forth herein.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

As used in the description of the invention and the appended claims, the singular forms "a", "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount of a compound (e.g., an amount of nornicotine) and the like, is meant to encompass variations of ±20%, ±10%, ±5%, ±1%, ±0.5%, or even ±0.1% of the specified amount.

NC EX90

The present invention includes tobacco cultivars, and parts thereof, from NC EX90. In another aspect, the present invention includes a tobacco plant, or part thereof, produced by growing the seed of NC EX90. A plant of the present invention can include a plant with essentially all of the morphological and physiological characteristics of cultivar NC EX90, when grown under the same environmental conditions.

While not being limited by process, NC EX90 is a result of the introduction of two mutated CYP82 genes in a Tennessee 90 Low Converter ("TN 90 LC") cultivar. The two genes are a mutated CYP82E4 gene recited as 325-6 #775 in Lewis et al. (Three nicotine demethylase genes mediate nornicotine biosynthesis in *Nicotiana tabacum* L.: Functional characterization of the CYP82E10 gene, *Phytochemistry* 71 (2010) 1988-1998 (SEQ ID NO: 1, which sets forth a cyp82e4 W329Stop, hereby incorporated by reference in its entirety)), and a mutated CYP82E5v2 recited in Lewis et al. (supra) as 325-6 #1-13 (SEQ ID NO: 2, which sets forth a cyp82e5v2 W422Stop, all references hereby incorporated by reference in their entirety). Both of these mutations result in truncated proteins. A cyp82e4 W329Stop and a cyp82e5v2 W422Stop are introduced from a e4e5l e4e5 double mutant in a strong converter burley background, line DH98-325-6, as listed in Table 2 of Lewis et al. (supra) into a TN 90 LC background.

NC EX90 is generated by backcrossing with TN 90 LC five times as the recurrent parent and selfing twice. NC EX90 is homozygous for both a cyp82e4 W329Stop and a cyp82e5v2 W422Stop. Again, not limited by any particular scientific theory, a cyp82e4 W329Stop and a cyp82e5v2 W422Stop are recessive. A cyp82e4 W329Stop and a cyp82e5v2 W422Stop encode proteins with reduced or eliminated ability to convert nicotine or nornicotine. NC EX90 has a genetic background that is at least 95%, at least 97%, at least 98%, or at least 99% similar to TN 90 LC. NC EX90 exhibits low NNN and is not subject to conversion to high NNN's. (See, FIG. 1)

NCBEX1MS

The present invention also provides tobacco cultivars, and parts thereof, from NCBEX1MS, where representative sample seeds of this cultivar have been deposited with the ATCC under ATCC Accession No. PTA-11719. The present invention also includes a tobacco plant, or part thereof, produced by growing a seed of NCBEX1MS. A plant of the present invention can include a plant with essentially all of the morphological and physiological characteristics of cultivar NCBEX1MS, when grown under the same environmental conditions. While not being limited by process, NCBEX1MS is a result of introducing the cyp82e4 W329Stop and cyp82e5v2 W422Stop mutations from NC EX90 BC$_5$F$_1$ into a TN 90 LC cytoplasmic male sterile ("CMS") plant by crossing NC EX90 BC$_5$F$_1$ as the male parent with TN 90 LC CMS to prepare CMS F$_1$ progeny plants.

The CMS F$_1$ progeny plants of the BC$_5$F$_1$×TN 90 LC CMS cross are male sterile. A plurality of BC$_5$F$_1$×TN 90 LC CMS F$_1$ plants (e.g., CMS F$_1$ progeny plants) are screened for the cyp82e4 W329Stop and cyp82e5v2 W422Stop mutations and crossed as the female parent to NC EX90 to prepare BC$_7$F$_1$ CMS progeny. BC$_7$F$_1$ CMS progeny homozygous for the cyp82e4 W329Stop and the cyp82e5v2 W422Stop mutations are identified by genotyping and designated as NCBEX1MS. NCBEX1MS has a genetic background that is at least 95%, at least 97%, at least 98%, or at least 99% similar to TN 90 LC. NCBEX1MS exhibits low NNN and is not subject to conversion to high NNN's.

NCBEX1F

The present invention also provides tobacco cultivars, and parts thereof, from NCBEX1F, representative sample seeds of this cultivar having been deposited with the ATCC under ATCC Accession No. PTA-11718. The present invention also includes a tobacco plant, or part thereof, produced by growing a seed of NCBEX1F. A plant of the present invention can further include a plant with essentially all of the morphological and physiological characteristics of cultivar NCBEX1F, when grown under the same environmental conditions. NCBEX1F is the result of seven backcrosses with TN 90 LC as the recurrent parent, followed by two rounds of selfing with selection for homozygosity for the cyp82e4 W329Stop and the cyp82e5v2 W422Stop mutations to yield $BC_7F_3$ plants. NCBEX1F has a genetic background that is at least 95%, at least 97%, at least 98%, or at least 99% similar to TN 90 LC. NCBEX1F exhibits low NNN and is not subject to conversion to high NNN's.

Other Plants

A progeny plant of the present application can be a plant of $F_1$, $F_2$, $F_3$, $F_4$ or later generation obtained by either crossing two parental plants or selfing one plant.

Under similar conditions as defined in the present application can be under similar environmental conditions or under similar laboratory conditions.

The present invention includes a tobacco seed produced by crossing two parent tobacco plants and harvesting the resultant tobacco seed, where at least one parent tobacco plant is NCBEX1F. In one aspect, the NCBEX1F is the male parent plant. In another aspect, the NCBEX1MS is the female parent plant. One aspect of the present invention provides tobacco plants that are homozygous at both a cyp82e4 and a cyp82e5v2 loci for SEQ ID NO: 1 and SEQ ID NO: 2, respectively, which share a genetic background that is greater than 75%, 80%, 85%, 90%, 95%, 98%, or 99% TN90 or TN90 LC. In one aspect, approximate or greater than 50%, 75%, or 100% of a progeny's genetics is provided by a plant of the present invention that is homozygous at both a cyp82e4 and a cyp82e5v2 loci for SEQ ID NO: 1 and SEQ ID NO: 2. In one aspect, a plant of the present invention has a genetic background that is at least 95%, at least 97%, at least 98%, or at least 99% similar to TN 90 LC. In another aspect, a plant of the present invention exhibits low NNN and is not subject to conversion to high NNN's. In one aspect, a plant of the present invention is the progeny plant of a female or male parent plant that is *Fusarium* wilt resistant.

In one aspect, a plant of the present invention is a medium-late maturing variety with moderately high yield potential. In another aspect, a plant of the present invention offers a broad range of important agronomic characteristics. In a further aspect, a plant of the present invention has one, two, three, four or more of the traits including moderate resistance to black shank, some tolerance to blue mold, black root rot resistance, and resistance to common virus diseases. In another aspect, a plant of the present invention has blue mold tolerance and level 4 resistance to both races of black shank and high root rot resistance. In one aspect, a plant of the present invention, such as NCBEX1F, NCBEX1MS, and NC EX90, lacks *Fusarium* wilt resistance. In another aspect, a plant of the present invention is *Fusarium* wilt resistant.

In an aspect, the plants of the present invention have reduced or eliminated ability to convert nicotine to nornicotine. In an aspect, the percentage nicotine conversion is less than about 75%, about 70%, about 60%, about 50%, or about 25% of that found in TN 90 LC or most other commercial burley tobacco cultivars grown and processed under similar conditions. The nicotine conversion in plants of the present invention, including NCBEX1F, NCBEX1MS, and NC EX90, can be less than about 4%, about 3.5%, about 3%, about 2.5%, about 2%, about 1.5%, about 1%, about 3-1%, about 3-0.5%, or about 2-0.5%. In a preferred aspect, the percentage nicotine conversion is less than about 25%, about 10%, about 5%, or about 2% of that found in TN90 without a cyp82e4 W329Stop and a cyp82e5v2 W422Stop. In an aspect, the tobacco plants of the present invention have a nicotine conversion rate of about 3.5, about 3.25, about 3.0 or about 2.75% or less. In another aspect, the nicotine conversion rate of tobacco plants of the present invention can be about 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, 0.5% or less. In another aspect, the nicotine conversion rate of tobacco plants of the present invention can be about 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6% or less. In another aspect, the nicotine conversion rates can be from about 0.5 to 0.9%, 0.5 to 1.5%, 0.5 to 2.0%, 0.5 to 2.5%, 0.5 to 2.75%, and 0.5 to 3.0%. In another aspect, the nicotine conversion rates can be from about 1.0 to 1.5%, 1.0 to 1.75%, 1.0 to 2.0%, 1.0 to 2.5%, 1.0 to 2.75%, and 1.0 to 3.0%. In another aspect, the nicotine conversion rate in a plant of the present invention may be less than about 2.9, 2.75, 2.5, 2.25, 2.0, 1.9, 1.8, 1.7, 1.6, 1.5, 1.4, 1.3, 1.2, 1.1 or 1.0%. In an aspect, the tobacco plants of the present invention have a nicotine conversion rate of 3.5, 3.25, 3.0 or 2.75% or less.

In another aspect, the tobacco plants of the present invention typically have a reduced amount of nornicotine of less than about 0.10% dry weight as compared to TN 90 LC or most other commercial burley tobacco cultivars grown and processed under similar conditions. For example, the nornicotine content in such plants can be about 1.2, 1.0, 0.7, 0.5, 0.4, 0.2, 0.1, 0.09, 0.085, 0.08, 0.075, 0.07, 0.065, 0.06, 0.055, 0.05, 0.045, 0.04, 0.035, 0.025, 0.01, 0.009, 0.0075, 0.005, 0.0025, 0.001, 0.0009, 0.00075, 0.0005, 0.00025, 0.0001% dry weight, or undetectable. In another aspect, the nornicotine content can be less than about 1.2, 1.0, 0.9, 0.8, 0.7, 0.5, 0.4, 0.2, 0.1, 0.075, 0.05, 0.025, 0.01, 0.009, 0.0075, 0.005, 0.0025, 0.001, 0.0009, 0.00075, 0.0005, 0.00025, 0.0001% dry weight. In another aspect, the nornicotine content in such plants can be from about 1.2-1.0, 0.7-0.5, 0.4-0.2, 0.1-0.075, 0.05-0.025, 0.01-0.0075, 0.005-0.0025, 0.001-0.00075, 0.0005-0.00025, or 0.0005-0.0001% dry weight. In a plant of the present invention, the nornicotine is a relatively small percentage of total alkaloids in the plant compared to a commercial seedlot of TN90 LC. The nornicotine in a plant of the present invention may be 2-1%, less than 3%, about 2%, about 1.5%, about 1%, or 0.75% percentage of total alkaloids.

Tobacco products having a reduced amount of nitrosamine content and/or more stably low nicotine conversion as compared to a product prepared from TN 90 LC or most other commercial burley tobacco cultivars grown and processed under similar conditions can be manufactured using tobacco plant material from plants and plant parts of the present invention. The tobacco product produced from a tobacco plant of this invention can have an amount of nornicotine of less than about 3 mg/g. For example, the nornicotine content in such a product can be about 3.0 mg/g, 2.5 mg/g, 2.0 mg/g, 1.5 mg/g, 1.0 mg/g, 750 µg/g, 500 pg/g, 250 pg/g, 100 pg/g, 75 pg/g, 50 pg/g, 25 pg/g, 10 pg/g, 7.0 pg/g, 5.0 pg/g, 4.0 pg/g, 2.0 pg/g, 1.0 pg/g, 0.5 pg/g, 0.4 pg/g, 0.2 pg/g, 0.1 pg/g, 0.05 pg/g, 0.01 pg/g, or undetectable. In some aspects, a tobacco product produced from a tobacco plant of this invention can have a amount of NNN of less than about 10 pg/g. For example, the NNN content in such a product can be about 10 pg/g, 7.0 pg/g, 5.0 pg/g, 4.0 pg/g, 2.0 pg/g, 1.0 pg/g, 0.5 pg/g, 0.4 pg/g, 0.2 pg/g, 0.1 pg/g, 0.05 pg/g, 0.01 pg/g, or undetectable. The percentage of secondary alkaloids relative to total alkaloid content contained in a plant of the present invention may not be statistically different than from a commercial seedlot of TN90 LC.

Differences between two inbred tobacco varieties or two hybrid tobacco varieties can be evaluated using statistical approaches. Statistical analysis includes the calculation of mean values, determination of the statistical significance of the sources of variation, and the calculation of the appropriate variance components. Methods for determining statistical significance are known in the art. Statistical software is available, for example, the PROC GLM function of SAS. Significance is generally presented as a "p-value". A statistically significant p-value is less than 0.10. In a preferred aspect, the p-value is less than, or equal to, 0.05. In another aspect, the p-value is 0.04 or less, 0.03 or less, 0.02 or less. In yet another aspect, a statistically significant value is less than 0.01. In yet another aspect, it can be less than 0.009, less than 0.008, less than 0.007, less than 0.006, less than 0.005, less than 0.004, less than 0.003, less than 0.002, or less than 0.001.

Tobacco plants of the present invention that are homozygous for cyp82e4 W329Stop and cyp82e5v2 W422Stop alleles have a reversion rate that is statistically significantly lower than corresponding control low-converter plants having wild type nicotine demethylase CYP82E4 and E5 genes. In addition, homozygous CYP82E4 and CYP82E5 double mutant tobacco plants have a percent conversion of nicotine to nornicotine of less than about 2.0%, e.g., undetectable to about 2.0%, about 1.0 to 2.0%, about 0.8 to 1.8%, about 0.8 to 2.0%, or about 1.0 to 2.0%.

Nicotine and nornicotine can be measured in ethylene-treated leaves using methods known in the art (e.g., gas chromatography). Percent nicotine demethylation in a sample is calculated by dividing the level of nornicotine by the combined level of nicotine and nornicotine as measured in the sample, and multiplying by 100. Percent nicotine demethylation in a sample from a plant of the present invention is 50, 40, 30, 20, 10 percent of a sample from an individual plant grown from a commercial seedlot of TN 90.

In an aspect, the tobacco plants of the present invention have a USDA quality index of about 73, about 72, about 71, about 70, about 69, about 68, about 67 or about 66. In an aspect, the tobacco plants of the present invention have a USDA quality index of about 65. In another aspect, the quality index may be at least about 55, 60, 62.5 or greater. In another aspect, tobacco plants of the present invention can have a quality index in the range of, about 60-65, about 60-70, about 62.5-65, about 62.5-70, or about 65-70, or any range therein.

A plant of the present invention, including NCBEX1MS, NCBEX1F, and NC EX90, can have any yield, including high (e.g., over 3000 lbs/A), moderately high (e.g., 2200-3000 lbs/A), and moderate (e.g., less than 2000 lbs/A) yield potential.

In another aspect, the present invention also provides for a plant grown from the seed of a NCBEX1F, NCBEX1MS, or NC EX90 plant in which alkaloids obtained from tobacco plants grown for the seed have decreased nornicotine and/or more stably low nicotine conversion as compared to TN 90 LC or most other commercial burley tobacco cultivars grown and processed under similar conditions, as well as plant parts and tissue cultures from such plants, representative sample seeds of these cultivars having been deposited with the ATCC, for example under ATCC Accession No. PTA-11718 for NCBEX1F and ATCC Accession No. PTA-11719 for NCBEX1MS.

An aspect of the present invention provides for parts of the cultivars NCBEX1F, NCBEX1MS, and NC EX90. For example, as used herein, a plant part includes but is not limited to leaves, pollen, embryos, cotyledons, hypocotyls, roots, root tips, anthers, flowers, ovules, shoots, stems, stalks, pith and capsules, petioles, pods, tissue culture comprising tissue, callus, cells or protoplasts of the cultivars NCBEX1F, NCBEX1MS, and/or NC EX90. In another aspect, the present invention provides for parts from hybrids having cultivars NCBEX1F, NCBEX1MS, and/or NC EX90 as parents or ancestors, and NCBEX1F, NCBEX1MS, and/or NC EX90 derived tobacco plants. In yet another aspect, the present invention provides for parts from genetically modified (e.g., by conventional breeding or genetic engineering techniques) forms of the foregoing plants and tissue culture.

Additional aspects of the present invention provide products comprising tobacco wherein the tobacco further comprises tobacco from the plants of the present invention, and parts thereof. Other aspects of the invention provide cured plant leaves and other plant parts from the plants of the present invention. Accordingly, in some aspects the cured plant parts include, but are not limited to, a leaf, pollen, ovule, embryo, cotyledon, hypocotyl, meristematic cell, protoplast, root, root tip, pistil, anther, flower, shoot, stem, pod, petiole, capsules and the like, and combinations thereof.

Thus, in some aspects, the present invention provides a cured tobacco comprising the leaves of the tobacco plant designated NCBEX1F, a representative sample seed of said cultivar having been deposited with the ATCC under ATCC Accession No. PTA-11718. In another aspect the present invention provides a cured tobacco comprising the leaves of the tobacco plant designated NCBEX1MS, a representative sample seed of said cultivar having been deposited with the ATCC under ATCC Accession No. PTA-11719. In yet another aspect, the present invention provides a cured tobacco comprising the leaves of the tobacco plant designated NC EX90.

In an aspect, the present invention provides a cured tobacco comprising the stems of the tobacco plant designated NCBEX1F, a representative sample seed of said cultivar having been deposited with the ATCC under ATCC Accession No. PTA-11718. In another aspect the present invention provides a cured tobacco comprising the stems of the tobacco plant designated NCBEX1MS, a representative sample seed of said cultivar having been deposited with the ATCC under ATCC Accession No. PTA-11719. In yet another aspect, the present invention provides a cured tobacco comprising the stems of the tobacco plant designated NC EX90.

In still other aspects, the present invention provides a cured tobacco comprising the leaves and stems of the tobacco plants designated NCBEX1F, NCBEX1MS, and/or NC EX90, representative sample seeds of these cultivars having been deposited with the ATCC under ATCC Accession No. PTA-11718 for NCBEX1F and ATCC Accession No. PTA-11719 for NCBEX1MS.

The present invention also provides a container of NCBEX1F, NCBEX1MS, or NC EX90 seeds or other seeds of the present invention (e.g., hybrids, inbreds, and the like) in which alkaloids obtained from tobacco plants grown from greater than 50% of the seeds have decreased nornicotine and/or more stably low nicotine conversion as compared to TN 90 LC or most other commercial burley tobacco cultivars grown under similar conditions. In another aspect, alkaloids obtained from NCBEX1F, NCBEX1MS, or NC EX90 plants or other plants of the present invention grown from greater than 55%, 60%, 65%, 70%, 75%, 80%, 85%, 90%, 95% of the seeds in the container have decreased nornicotine and/or more stably low nicotine conversion as compared to TN 90 LC or most other commercial burley tobacco cultivars grown under similar conditions, representative sample seeds of cultivars NCBEX1F and NCBEX1MS having been deposited with the ATCC under ATCC Accession No. PTA-11718 for NCBEX1F and ATCC Accession No. PTA-11719 for NCBEX1MS.

A container of NCBEX1F, NCBEX1MS, or NC EX90 seeds or other seeds of the present invention may contain any number, weight or volume of seeds. For example, a container can contain at least, or greater than, about 100, 200, 300, 400, 500, 600, 700, 800, 900, 1000, 1500, 2000, 2500, 3000, 3500, 4000 or more seeds. Alternatively, the container can contain at least, or greater than, about 1 ounce, 5 ounces, 10 ounces, 1 pound, 2 pounds, 3 pounds, 4 pounds, 5 pounds or more seeds. Representative sample seeds of NCBEX1F and NCBEX1MS cultivars having been deposited with the ATCC under ATCC Accession Nos. PTA-11718 and PTA-11719, respectively.

Containers of NCBEX1F, NCBEX1MS, or NC EX90 seeds or other seeds of the present invention may be any container available in the art. By way of a non-limiting example, a container may be a box, a bag, a packet, a pouch, a tape roll, a pail, a foil, or a tube, representative sample seeds of these cultivars having been deposited with the ATCC. Representative sample seeds of NCBEX1F and NCBEX1MS cultivars have been deposited with the ATCC under ATCC Accession Nos. PTA-11718 and PTA-11719, respectively.

In another aspect, the present invention also provides a container of NCBEX1F, NCBEX1MS, or NC EX90 seeds in which greater than 50% of NCBEX1F, NCBEX1MS, or NC EX90 seeds or other seeds of the present invention have decreased nornicotine and/or more stably low nicotine conversion as compared to TN 90 LC or most other commercial burley tobacco cultivars grown and processed under similar conditions. Representative sample seeds of NCBEX1F and NCBEX1MS cultivars have been deposited with the ATCC under ATCC Accession Nos. PTA-11718 and PTA-11719, respectively.

In one aspect, the present invention provides a seed of a NCBEX1F, NCBEX1MS, or NC EX90 plant or other plant of the present invention in which a plant grown from the seed is male sterile. Representative sample seeds of NCBEX1F and NCBEX1MS cultivars have been deposited with the ATCC under ATCC Accession Nos. PTA-11718 and PTA-11719, respectively.

Tobacco material, including without limitation any plant parts, for example leaves, midveins, and stalks, obtained from the tobacco cultivars, lines, varieties or hybrids of the present invention can be used to make tobacco products including, without limitation, cigarette products (e.g., cigarettes and bidi cigarettes), cigar products (e.g., cigar wrapping tobacco and cigarillos), pipe tobacco products, smokeless cigarette products, smokeless tobacco products (e.g., moist snuff, dry snuff, and chewing tobacco), films, chewables, tabs, shaped parts, gels, consumable units, insoluble matrices, hollow shapes and the like. See e.g., U.S. Patent Publication No. US 2006/0191548, which is herein incorporated by reference in its entirety.

Tobacco products derived from plants of the present invention also include cigarettes and other smoking articles, particularly those smoking articles including filter elements, wherein the rod of smokeable material includes cured tobacco within a tobacco blend. In an aspect, a tobacco product may be pipe tobacco, cigar tobacco, cigarette tobacco, chewing tobacco, leaf tobacco, shredded tobacco, and cut tobacco.

In an aspect, the tobacco product of the present invention can be a blended tobacco product. In other aspects of the invention, the tobacco product of the present invention can be a reduced nicotine tobacco product. In still other aspects, the tobacco product of the present invention can be a blended tobacco product with reduced nicotine content. Thus, the tobacco product of the present invention can be a blended reduced nicotine tobacco product. Tobacco product material comprises a blend of tobacco materials from the present invention, wherein the blend comprises at least about 5, 10, 20, 30, 40, 50, 60, 70, 80, 90, or 95 percent by weight of a cured tobacco, based on the dry weight of the tobacco material. US 2008/0245377 is herein incorporated by reference for blend mixtures in its entirety.

In an aspect, tobacco products having a reduced amount of nitrosamine content can be manufactured using tobacco plant material from plants and/or plant parts of the present invention. The tobacco product typically has a reduced amount of nornicotine of less than about 3 mg/g as compared to a product prepared from TN 90 LC or most other commercial burley tobacco cultivars grown and processed under similar conditions. For example, the nornicotine content in such a product can be 3.0 mg/g, 2.5 mg/g, 2.0 mg/g, 1.5 mg/g, 1.0 mg/g, 750 µg/g, 500 pg/g, 250 pg/g, 100 pg/g, 75 pg/g, 50 pg/g, 25 pg/g, 10 pg/g, 7.0 pg/g, 5.0 pg/g, 4.0 pg/g, 2.0 pg/g, 1.0 pg/g, 0.5 pg/g, 0.4 pg/g, 0.2 pg/g, 0.1 pg/g, 0.05 pg/g, 0.01 pg/g, or undetectable. The tobacco product comprising tobacco material from a plant or plant part thereof of this invention typically has a reduced amount of NNN of less than about 10 pg/g as compared to a product prepared from TN 90 LC or most other commercial burley tobacco cultivars grown and processed under similar conditions. For example, the nornicotine content in such a product can be about 10 pg/g, 7.0 pg/g, 5.0 pg/g, 4.0 pg/g, 2.0 pg/g, 1.0 pg/g, 0.5 pg/g, 0.4 pg/g, 0.2 pg/g, 0.1 pg/g, 0.05 pg/g, 0.01 pg/g, or undetectable. The percentage of secondary alkaloids relative to total alkaloid content contained in a plant of the present invention may not be statistically different than from a commercial seedlot of TN90 LC.

A tobacco plant of the present invention designated NCBEX1F, NCBEX1MS, or NC EX90, carrying cyp82e4 W329Stop and cyp82e5v2 W422Stop alleles can be used in a plant breeding program to create useful lines, cultivars, varieties, progeny, inbreds, and/or hybrids. Thus, in some aspects, an $F_1$, $F_2$, $F_3$, or later generation tobacco plant containing cyp82e4 W329Stop and cyp82e5v2 W422Stop alleles is crossed with a second *Nicotiana* plant, and progeny of the cross are identified in which the cyp82e4 W329Stop and cyp82e5v2 W422Stop alleles are present. It will be appreciated that the second *Nicotiana* plant will be TN90 or TN90 LC, optionally with an additional desirable trait. In some aspects the additional desirable trait can be herbicide resistance mentioned below. It will also be appreciated that the second TN90 or TN90 LC *Nicotiana* plant can contain cyp82e4 W329Stop and cyp82e5v2 W422Stop alleles.

In still other aspects, methods of the present invention further include self-pollinating or pollinating a male sterile pollen acceptor with a pollen donor capable of being used in production of a progeny plant of the present invention, such as a male sterile hybrid of the present invention. Either the male sterile pollen acceptor plant or the pollen donor plant has at least one mutant allele, preferably two, at a nicotine demethylase locus, such as cyp82e4 W329Stop and cyp82e5v2 W422Stop. In an aspect, both alleles at each nicotine demethylase locus are mutant alleles, making the plant homozygous for cyp82e4 W329Stop and cyp82e5v2 W422Stop.

Breeding can be carried out via any known procedures. DNA fingerprinting, SNP or similar technologies may be used in a marker-assisted selection (MAS) breeding program to transfer or breed mutant alleles of a nicotine demethylase gene into other tobaccos. For example, a breeder can create segregating populations from hybridizations of a genotype containing cyp82e4 W329Stop and cyp82e5v2 W422Stop alleles with an agronomically desirable genotype. Plants in the $F_2$ or backcross generations can be screened using a marker developed from cyp82e4 W329Stop or cyp82e5v2 W422Stop alleles or a fragment thereof, using one of the techniques known in the art or listed herein. Plants identified as possessing cyp82e4 W329Stop and cyp82e5v2 W422Stop alleles can be backcrossed or self-pollinated to create a second population to be screened. Depending on the expected inheritance pattern or the MAS technology used, it may be necessary to self-pollinate the selected plants before each cycle of backcrossing to aid identification of the desired individual plants. Backcrossing or other breeding procedure can be repeated until the desired phenotype of the recurrent parent is recovered. A recurrent parent in the present invention can be NCBEX1F or NC EX90. Other breeding techniques can be found, for example, in Wernsman, E. A., and Rufty, R. C. 1987. Chapter Seventeen. Tobacco. Pages 669-698 In: Cultivar Development. Crop Species. W. H. Fehr (ed.), MacMillan Publishing Go., Inc., New York, N.Y., incorporated herein by reference in their entirety.

*Nicotiana* species which exhibit breeding compatibility with *Nicotiana tabacum* include *Nicotiana amplexicaulis*, PI 271989; *Nicotiana benthamiana* PI 555478; *Nicotiana bigelovii* PI 555485; *Nicotiana debneyi*; *Nicotiana excelsior* PI 224063; *Nicotiana glutinosa* PI 555507; *Nicotiana goodspeedii* PI 241012; *Nicotiana gossei* PI 230953; *Nicotiana hesperis* PI 271991; *Nicotiana knightiana* PI 555527; *Nicotiana maritima* PI 555535; *Nicotiana megalosiphon* PI 555536; *Nicotiana nudicaulis* PI 555540; *Nicotiana paniculata* PI 555545; *Nicotiana plumbaginifolia* PI 555548; *Nicotiana repanda* PI 555552; *Nicotiana rustica*; *Nicotiana suaveolens* PI 230960; *Nicotiana sylvestris* PI 555569; *Nicotiana tomentosa* PI 266379; *Nicotiana tomentosiformis*; and *Nicotiana trigonophylla* PI 555572. See also, Compendium of Tobacco Diseases published by American Phytopathology Society, or The Genus *Nicotiana* Illustrated, published by Japan Tobacco Inc, hereby incorporated by reference in their entirety.

The result of a plant breeding program using the tobacco plants described herein includes useful lines, cultivars, varieties, progeny, inbreds, and hybrids. As used herein, the term 'variety' refers to a population of plants that share constant characteristics which separate them from other plants of the same species. A variety is often, although not always, sold commercially. While possessing one or more distinctive traits, a variety is further characterized by a very small overall variation between individuals within that variety. A 'pure line' variety may be created by several generations of self-pollination and selection, or vegetative propagation from a single parent using tissue or cell culture techniques. A variety can be essentially derived from another line or variety. As defined by the International Convention for the Protection of New Varieties of Plants (Dec. 2, 1961, as revised at Geneva on Nov. 10, 1972, on Oct. 23, 1978, and on Mar. 19, 1991), a variety is 'essentially derived' from an initial variety if: a) it is predominantly derived from the initial variety, or from a variety that is predominantly derived from the initial variety, while retaining the expression of the essential characteristics that result from the genotype or combination of genotypes of the initial variety; b) it is clearly distinguishable from the initial variety; and c) except for the differences which result from the act of derivation, it conforms to the initial variety in the expression of the essential characteristics that result from the genotype or combination of genotypes of the initial variety. Essentially derived varieties can be obtained, for example, by the selection of a natural or induced mutant, a somaclonal variant, a variant individual from plants of the initial variety, backcrossing, or transformation. A 'line' as distinguished from a variety most often denotes a group of plants used non-commercially, for example in plant research. A line typically displays little overall variation between individuals for one or more traits of interest, although there may be some variation between individuals for other traits.

Hybrid tobacco varieties can be produced by preventing self-pollination of female parent plants (i.e., seed parents) of a first variety, permitting pollen from male parent plants of a second variety to fertilize the female parent plants, and allowing $F_1$ hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by cytoplasmic male sterility (CMS), or transgenic male sterility wherein a transgene inhibits microsporogenesis and/or pollen formation, or self-incompatibility. Female parent plants containing CMS are particularly useful. In aspects in which the female parent plants are CMS, pollen may be harvested from male fertile plants and applied manually to the stigmas of CMS female parent plants, and the resulting $F_1$ seed harvested.

Plants can be used to form single-cross tobacco $F_1$ hybrids. In such an aspect, the plants of the parent varieties can be grown as substantially homogeneous adjoining populations to facilitate natural cross-pollination from the male parent plants to the female parent plants. The $F_1$ seed formed on the female parent plants is selectively harvested by conventional means. One also can grow the two parent plant varieties in bulk and harvest a blend of $F_1$ hybrid seed formed on the female parent and seed formed upon the male parent as the result of self-pollination. Alternatively, three-way crosses can be carried out wherein a single-cross $F_1$ hybrid is used as a female parent and is crossed with a different male parent. As another alternative, double-cross hybrids can be created wherein the $F_1$ progeny of two different single-crosses are themselves crossed. Self-incompatibility can be used to particular advantage to prevent self-pollination of female parents when forming a double-cross hybrid.

In some aspects, successful crosses yield $F_1$ plants that are fertile, have cyp82e4 W329Stop and cyp82e5v2 W422Stop alleles, and can be backcrossed with one of the parents, such as NCBEX1F or NC EX90 if desired. In some aspects, a plant population in the $F_2$ generation is screened for cyp82e4 W329Stop and cyp82e5v2 W422Stop alleles. Selected plants can be crossed with one of the parents and the first backcross (BC1) generation plants are self-pollinated to produce a BC1 $F_2$ population that is again screened for variant nicotine demethylase gene expression (e.g., the null version of the nicotine demethylase gene). The process of backcrossing, self-pollination, and screening is repeated, for example, at least 4 times, until the final screening produces a plant that is fertile and reasonably similar to the recurrent parent. This plant, if desired, is self-pollinated and the progeny are subsequently screened again to confirm that the plant exhibits the same low and stable nicotine conversion phenotype as NCBEX1F. Breeder's seed of the selected plant is produced using standard methods including, for example, field testing, confirmation of the null condition for nicotine demethylase, chemical analyses of cured leaf to determine the level of alkaloids and/or chemical analyses of cured leaf to determine the ratio of nornicotine to nicotine+nornicotine.

In one aspect, a $F_1$ progeny is the result of a cross between NCBEX1F and NCBEX1MS to generate $F_1$ progeny that are male sterile. Male sterile tobacco plants may be produced by any method known in the art. Methods of producing male sterile tobacco are described in Wernsman, E. A., and Rufty, R. C. 1987. Chapter Seventeen. Tobacco. Pages 669-698 In: Cultivar Development. Crop Species. W. H. Fehr (ed.), Mac-Millan Publishing Go., Inc., New York, N.Y. 761 pp.

The present invention further provides methods of producing a tobacco plant by crossing one of cultivars NCBEX1F, NCBEX1MS, and/or NC EX90 with itself or a different tobacco line. The invention further relates to methods for producing other tobacco cultivars or breeding lines derived from cultivars NCBEX1F, NCBEX1MS, and/or NC EX90 by crossing a plant of a cultivar of NCBEX1F, NCBEX1MS, and/or NC EX90 with a second tobacco plant and growing the progeny seed to yield a NCBEX1F-, NCBEX1MS-, or NC EX90-derived tobacco plant. An additional aspect of the present invention provides a method for producing a tobacco plant that contains in its genetic material one or more transgenes, comprising crossing cultivars of the present invention with a second tobacco plant containing one or more transgenes to produce progeny that comprise the transgene(s) optionally operably linked to one or more regulatory elements. In one aspect, the second cultivar may be a plant derived from cultivars NCBEX1F, NCBEX1MS, and/or NC EX90 transformed with one or more transgenes.

The invention further provides for the vegetative propagation of a plant of cultivars NCBEX1F, NCBEX1MS, and/or NC EX90, hybrids and progeny thereof. In one aspect, the invention provides for a method of vegetatively propagating a plant of a tobacco cultivar comprising cultivating tissue capable of being propagated from a plant of a plant of cultivars NCBEX1F, NCBEX1MS, and/or NC EX90, to obtain a proliferated shoot and rooting the proliferated shoots to obtain a rooted plantlet. In another aspect, the plant tissue may be from an $F_1$ hybrid of a plant of cultivars NCBEX1F, NCBEX1MS, and/or NC EX90. In an aspect, the plant tissue may be from an $F_2$, $F_3$, $F_4$ or later progeny plant obtained by breeding a plant of cultivars NCBEX1F, NCBEX1MS, and/or NC EX90.

A plant comprising a mutation in a nicotine demethylase gene can be identified by selecting or screening the mutagenized plant material, or progeny thereof. Such screening and selection methodologies are known to those having ordinary skill in the art. Examples of screening and selection methodologies include, but are not limited to, Southern analysis, PCR amplification for detection of a polynucleotide, Northern blots, RNase protection, primer-extension, RT-PCR amplification for detecting RNA transcripts, enzymatic assays for detecting enzyme or ribozyme activity of polypeptides and polynucleotides, and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known.

It is understood that a tobacco plant of the present invention, including NCBEX1F, NCBEX1MS and/or NC EX90, can be transformed by a genetic construct or transgene using a technique known in the art. Without limitation, an example of a desired trait is herbicide resistance, pest resistance, disease resistance; high yield; high grade index; curability; curing quality; mechanical harvestability; holding ability; leaf quality; height, plant maturation (e.g., early maturing, early to medium maturing, medium maturing, medium to late maturing, or late maturing); stalk size (e.g., a small, medium, or a large stalk); or leaf number per plant (e.g., a small (e.g., 5-10 leaves), medium (e.g., 11-15 leaves), or large (e.g., 16-21) number of leaves), or any combination thereof. Any plant of the present invention can be used as a basis for tissue culture, regenerated, transformed, or a combination of any of these. In an aspect, a plant of the present invention derived by tissue culture, transformation, or both has essentially all of the morphological and physiological characteristics of cultivar NCBEX1F, NCBEX1MS or NC EX90 under similar conditions.

Having now generally described the invention, the same will be more readily understood through reference to the following examples that are provided by way of illustration, and are not intended to be limiting of the present invention, unless specified.

EXAMPLES

Example 1

Breeding of Homozygous cyp82e4 W329Stop and cyp82e5v2 W422Stop Mutant Plants into the TN 90 LC Background NC EX90 is a backcross-derived version of burley tobacco cultivar TN 90 LC carrying introduced deleterious mutations in cyp82e4 and cyp82e5v2, two genes previously documented to encode for nicotine demethylase enzymes (Lewis et al., supra). To prepare NC EX90 an individual plant grown from a commercial seedlot of TN 90 LC is selected and initially crossed with plant GH08B-14 in a greenhouse. GH08B-14 is a burley tobacco cultivar heterozygous for the cyp82e4 W329Stop and the cyp82e5v2 W422Stop mutations described by Lewis et al. (2010). A plurality of $F_1$ plants are screened for the presence of the cyp82e4 W329Stop and the cyp82e5v2 W422Stop mutations. Individual $F_1$ plants are selected and backcrossed to TN 90 LC in a greenhouse to produce $BC_1F_1$ progeny. A plurality of $BC_1F_1$ progeny are screened and an individual plant heterozygous for the cyp82e4 W329Stop and cyp82e5v2 W422Stop mutations is identified. The heterozygous selected $BC_1F_1$ plant is backcrossed to TN 90 LC in a greenhouse to produce $BC_2F_1$ seed. A plurality of $BC_2F_1$ plants are screened for the presence of the cyp82e4 W329Stop and cyp82e5v2 W422Stop mutations to identify a heterozygous progeny plant for a subsequent round of backcross breeding. Using this backcross procedure, individual heterozygous plants having the cyp82e4 W329Stop and cyp82e5v2 W422Stop mutations are identified in the $BC_3F_1$, $BC_4F_1$, and $BC_5F_1$ progeny.

To produce plants homozygous for the cyp82e4 W329Stop and cyp82e5v2 W422Stop mutations, $BC_5F_1$ progeny plants are screened for the cyp82e4 W329Stop and cyp82e5v2 W422Stop mutations to identify heterozygous plants. Individual plants heterozygous for the cyp82e4 W329Stop and cyp82e5v2 W422Stop mutations are self-pollinated to produce $BC_5F_2$ seed. A plurality of $BC_5F_2$ progeny are genotyped to identify individuals homozygous for both of the cyp82e4 W329Stop and the cyp82e5v2 W422Stop mutations. Four individual $BC_5F_2$ progeny plants are self-pollinated to produce four $BC_5F_3$ progeny lines. $BC_5F_3$ are homozygous for the CYP82E4 W329Stop and CYP82E5v2 W422Stop mutations.

Identification of $BC_5F_3$ Progeny Lines with Desirable Traits

Plants from the four $BC_5F_3$ progeny lines are grown in a randomized complete block design with three replications for evaluation of cured leaf chemistry, yield, and physical quality at three North Carolina field research locations during 2010 (Waynesville, Laurel Springs, and Reidsville). Each replicated block is a 20-plant plot. Plants are stalk cut at maturity, air cured and evaluated by a former USDA tobacco grader. Plot weights are used to determine per acre yields. Fifty gram composite leaf samples are collected from each plot and analyzed for percent nicotine, nornicotine, anatabine, and anabasine by gas chromatography. $BC_5F_3$ progeny line #3 is identified with superior yield, high grade and desirable alkaloid content and designated 'NC EX90.'

Analysis of NC EX90

Results of gas chromatography alkaloid analysis are presented in Table 1.

Analysis with single degree of freedom CONTRAST statements are performed using the PROC GLM function of SAS. This line exhibits significantly lower levels of nornicotine (P<0.0001) and nicotine conversion (P=0.0002) as compared to a commercial seedlot of TN 90 LC (Table 1). The ratio of secondary alkaloids to total alkaloids are significantly lower for NC EX90 relative to TN 90 LC (P=0.0071). The two lines are not significantly different for nicotine, anatabine, anabasine, yield, or cured leaf quality.

Example 3

Preparation of Cytoplasmic Male Sterile Lines

To prepare a cytoplasmic male sterile (CMS) line, a $BC_5F_1$ progeny plant prepared as described in Example 1 above that is heterozygous for the cyp82e4 W329Stop and the cyp82e5v2 W422Stop mutations is selected and crossed as the pollen parent to a proprietary CMS sterile line of the North Carolina State University designated TN 90 LC CMS. TN 90 LC CMS is prepared by crossing a TN 90 LC plant with a plant of tobacco species *Nicotiana suaveolens*. The $F_1$ progeny plant is backcrossed nine times to TN 90 LC to produce $BC_9F_1$ plants and designated TN 90 LC CMS. The TN 90 LC CMS line is maintained by backcrossing to TN 90 LC.

The $F_1$ progeny plants of the $BC_5F_1 \times$ TN 90 LC CMS are male sterile. A plurality of $BC_5F_1 \times$ TN 90 CMS $F_1$ plants (e.g., the $F_1$ progeny plants) are screened for the cyp82e4 W329Stop and the cyp82e5v2 W422Stop mutations and crossed as the female parent to TN 90 LC to prepare $BC_7F_1$ CMS progeny. $BC_7F_1$ CMS progeny heterozygous for the cyp82e4 W329Stop and the cyp82e5v2 W422Stop mutations

TABLE 1

Comparisons between TN 90 LC and NC EX90 (TN 90 LC + e4e4 + e5e5) for alkaloid determinations, yield, and cured leaf quality.

| Entry | Nicotine (% dry weight) | Nornicotine (% dry weight) | Anatabine (% dry weight) | Anabasine (% dry weight) | Total Alkaloids (% dry weight) | Nicotine Conversion (%) | Ratio Secondary Alkaloids: Total Alkaloids | Yield (lbs/A) | Quality Index |
|---|---|---|---|---|---|---|---|---|---|
| TN 90 LC | 3.579 | 0.158 | 0.216 | 0.022 | 3.980 | 3.918 | 0.096 | 2403.3 | 62.59 |
| NC EX90 | 3.571 | 0.076 | 0.221 | 0.022 | 3.890 | 2.043 | 0.081 | 2454.5 | 65.70 |
| P-value[a] | 0.9622 | <0.0001 | 0.7560 | 0.7059 | 0.6620 | 0.0002 | 0.0071 | 0.8856 | 0.5514 |

[a]P-values were obtained from single degree of freedom CONTRAST statements executed by PROC GLM of SAS.
Means are from three 2010 North Carolina environments. The experimental design at each location was a randomized complete block design with three replications.

Example 2

Preparation of Inbred Line NCBEX1F

To prepare inbred line NCBEX1F, two additional rounds of backcrossing of individual $BC_5F_1$ progeny plants prepared in Example 1 above are performed. A plurality of $BC_5F_1$ plants are screened for the presence of the cyp82e4 W329Stop and the cyp82e5v2 W422Stop mutations to identify a heterozygous progeny plant for a subsequent round of backcross breeding. Using this backcross procedure, individual heterozygous plants having the cyp82e4 W329Stop and the cyp82e5v2 W422Stop mutations are identified in the $BC_6F_1$ and $BC_7F_1$ progeny.

To produce plants homozygous for the cyp82e4 W329Stop and the cyp82e5v2 W422Stop mutations, $BC_7F_1$ progeny plants are screened for the cyp82e4 W329Stop and the cyp82e5v2 W422Stop mutations to identify heterozygous plants. Individual plants heterozygous for the cyp82e4 W329Stop and the cyp82e5v2 W422Stop mutations are self-pollinated to produce $BC_7F_2$ seed. A plurality of $BC_7F_2$ progeny are genotyped to identify individuals homozygous for both of the cyp82e4 W329Stop and the cyp82e5v2 W422Stop mutations. Individual $BC_7F_2$ progeny plants are self-pollinated to produce individual $BC_7F_3$ progeny lines. The NCBEX1F progeny lines are homozygous for the cyp82e4 W329Stop and the cyp82e5v2 W422Stop mutations.

are identified by genotyping. Two rounds of crossing to NC EX90 are performed to prepare $BC_7F_3$ CMS plants and designated as line NCBEX1MS. To maintain the line, plants of line NCBEX1MS plants are pollinated with a NCBEX1F plant.

Example 4

Figure 2A:
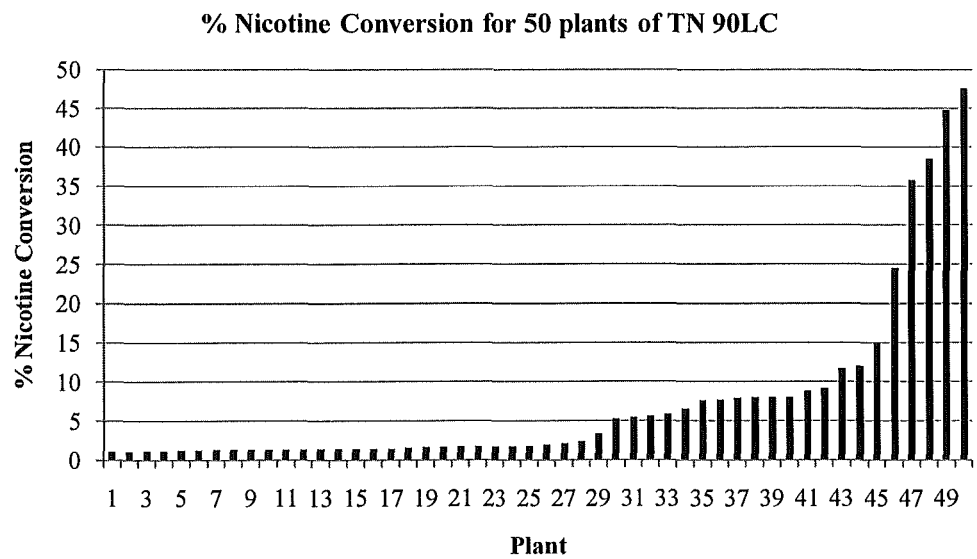
FIGS. 2A and 2B set forth the percentage of nicotine conversion for 50 plants of TN 90 LC and NCBEX1MS, respectively.
Figure 2B:
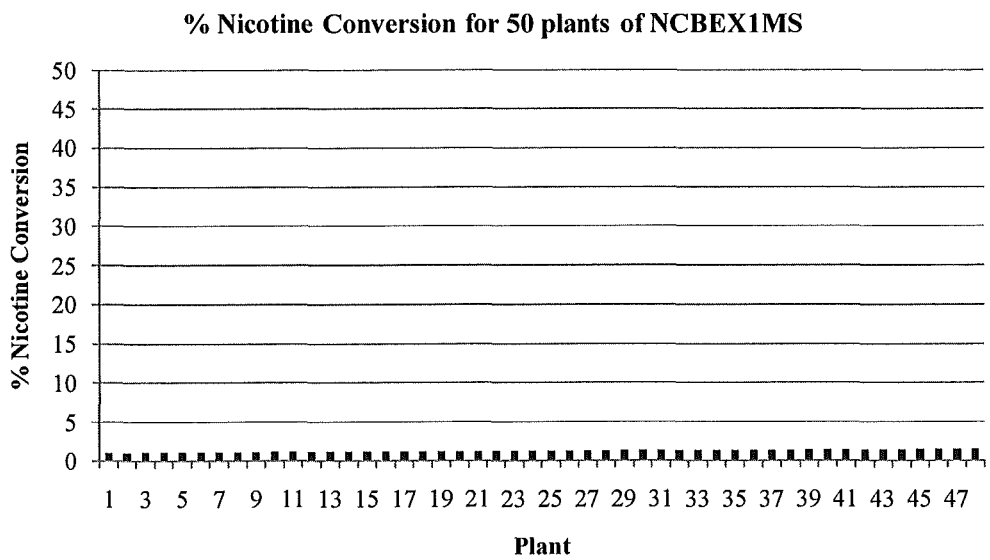

Demonstration of Trait Stability in Nicotine Conversion for NCBEX1Ms Relative to TN 90LC Leaves from 50 plants for NCBEX1MS and TN90LC are collected using the "LC" method as disclosed in Jack et al. Implications of reducing nornicotine accumulation in burley tobacco: Appendix A—The LC Protocol. *Rec. Adv. Tob. Sci.* 2007, 33, 58-79. Leaves are air cured and analyzed for alkaloid profiles using gas chromatography. See FIGS. 2A and 2B and Table 2.

Analysis with single degree of freedom CONTRAST statements are performed using the PROC GLM function of SAS. This line exhibits significantly lower levels of nornicotine (P<0.05) and nicotine conversion (P<0.05) as compared to a commercial seedlot of TN 90 LC. Rates of nicotine conversion and nornicotine levels are significantly reduced while yield and quality of NCBEX1MS lines is not significantly different from TN 90 LC (differences do not exceed the LSD at the 0.05 level of significance).

TABLE 2

Comparison of NCBEX1MS relative to TN 90 LC and standard checks for yield, quality, and cured leaf chemistry during the 2011 growing season.

| Genotype | Yield (lbs/A) | Grade Index | Nicotine (%) | Nornicotine (%) | Anabasine (%) | Anatabine (%) | Nicotine Conversion (%) |
|---|---|---|---|---|---|---|---|
| VA509 | 2959.3 | 69.3 | 3.405 | 0.155 | 0.014 | 0.151 | 4.297 |
| Ky 14 LC | 3126.2 | 71.9 | 3.644 | 0.086 | 0.016 | 0.187 | 2.256 |
| TN 90 LC (certified) | 3139.7 | 70.7 | 3.845 | 0.159 | 0.016 | 0.220 | 3.932 |
| NCBEX1MS | 3142.9 | 72.2 | 3.955 | 0.080 | 0.016 | 0.200 | 1.971 |
| LSD (0.05) | 473.5 | 8.4 | 0.570 | 0.053 | 0.004 | 0.054 | 1.085 |

Means are averages over three 2011 field environments. The experimental design was a randomized complete block design with four replications at each environment.

DEPOSIT INFORMATION

A deposit of at least 2500 seeds of the proprietary inbred plant lines disclosed above and recited in the appended claims have been made with American Type Culture Collection (ATCC), 10801 University Boulevard, Manassas, Va. 20110. The date of deposit for NCBEX1F and NCBEX1MS was Sep. 6, 2011 and Sep. 6, 2011, respectively. The deposit of 2500 seeds for each variety was taken from the same deposit maintained since prior to the filing date of this application. Upon issuance of a patent, all restrictions upon the deposit will be removed, and the deposit is intended to meet all of the requirements of 37 C.F.R. §1.801-1.809. The ATCC accession numbers for inbred lines NCBEX1F and NCBEX1MS are PTA-11718, PTA-11719, respectively. These deposits will be maintained in the depository for a period of 30 years, or 5 years after the last request, or for the effective life of the patent, whichever is longer, and will be replaced as necessary during that period. Applicants do not waive any infringement of their rights granted under this patent or under the Plant Variety Protection Act (7 U.S.C. 2321 et seq.).

What is claimed is:

1. A seed of tobacco cultivar NCBEX1F, a tobacco cultivar essentially derived from said tobacco cultivar NCBEX1F, or a tobacco hybrid produced from said tobacco cultivar NCBEX1F, wherein said seed comprises SEQ ID NO: 1 and SEQ ID NO: 2, a representative sample seed of said cultivar NCBEX1F is deposited with the ATCC under ATCC Accession No. PTA-11718, wherein said tobacco cultivar NCBEX1F, said tobacco cultivar essentially derived from said tobacco cultivar NCBEX1F, and said tobacco hybrid produced from said tobacco cultivar NCBEX1F comprises a percent nicotine conversion less than about 2.5%.

2. A tobacco plant, or a part thereof, produced by growing the seed of claim 1, wherein said part is selected from the group consisting of leaf, pollen, ovule, embryo, cotyledon, hypocotyl, meristematic cell, protoplast, root, root tip, pistil, anther, flower, shoot, stem, pod and petiole.

3. A harvested leaf of the tobacco plant of claim 2.

4. The harvested leaf of claim 3, wherein said leaf has a reduced amount of nornicotine when compared to a leaf from TN90 LC.

5. The harvested leaf of claim 4, wherein said reduced amount of nornicotine is reduced in a smoke stream produced from burning said leaf.

6. A tobacco product, comprising tobacco material prepared from the tobacco plant, or part thereof, of claim 2.

7. The tobacco product of claim 6, wherein said product is selected from the group consisting of a cigarillo, a non-ventilated recess filter cigarette, a vented recess filter cigarette, a cigar, snuff, pipe tobacco, cigar tobacco, cigarette tobacco, leaf tobacco, shredded tobacco, cut tobacco, and chewing tobacco.

8. The tobacco product of claim 7, wherein said product has a reduced amount of nornicotine when compared to a tobacco product made from TN90 LC.

9. A seed of tobacco cultivar NCBEX1MS, a tobacco cultivar essentially derived from said tobacco cultivar NCBEX1MS, or a tobacco hybrid produced from tobacco cultivar NCBEX1MS, wherein said seed comprises SEQ ID NO: 1 and SEQ ID NO: 2, a representative sample seed of said cultivar NCBEX1MS is deposited with the ATCC under ATCC Accession No. PTA-11719, wherein said tobacco cultivar NCBEX1MS, said tobacco cultivar essentially derived from said tobacco cultivar NCBEX1MS, and said tobacco hybrid produced from said tobacco cultivar NCBEX1MS comprises a percent nicotine conversion less than about 2.5%.

10. A tobacco plant, or a part thereof, produced by growing the seed of claim 9, wherein said part is selected from the group consisting of leaf, pollen, ovule, embryo, cotyledon, hypocotyl, meristematic cell, protoplast, root, root tip, pistil, anther, flower, shoot, stem, pod and petiole.

11. A harvested leaf of the tobacco plant of claim 10.

12. The harvested leaf of claim 11, wherein said leaf has a reduced amount of nornicotine when compared to a leaf from TN90 LC.

13. The harvested leaf of claim 12, wherein said reduced amount of nornicotine is reduced in a smoke stream produced from burning said leaf.

14. A tobacco product, comprising tobacco material prepared from the tobacco plant, or part thereof, of claim 10.

15. The tobacco product of claim 14, wherein said product is selected from the group consisting of a cigarillo, a non-ventilated recess filter cigarette, a vented recess filter cigarette, a cigar, snuff, pipe tobacco, cigar tobacco, cigarette tobacco, leaf tobacco, shredded tobacco, cut tobacco, and chewing tobacco.

16. The tobacco product of claim 15, wherein said product has a reduced amount of nornicotine when compared to a tobacco product made from TN90 LC.

17. An $F_2$ progeny plant of tobacco cultivar NCBEX1F, wherein said $F_2$ progeny plant comprises SEQ ID NO: 1 and SEQ ID NO: 2, a representative sample seed of said cultivar is deposited with the ATCC under ATCC Accession No. PTA-11718 wherein said $F_2$ progeny plant comprises a percent nicotine conversion less than about 2.5%.

18. An $F_2$ progeny plant of tobacco cultivar NCBEX1MS, wherein said $F_2$ progeny plant comprises SEQ ID NO: 1 and SEQ ID NO: 2, a representative sample seed of said cultivar is deposited with the ATCC under ATCC Accession No. PTA-11719 wherein said $F_2$ progeny plant comprises a percent nicotine conversion less than about 2.5%.

19. The $F_2$ progeny plant of claim 17, wherein said $F_2$ progeny plant is male sterile (MS).

20. The $F_2$ progeny plant of claim 18, wherein said $F_2$ progeny plant is male sterile (MS).

21. The tobacco product of claim 6, wherein said tobacco product is prepared from said tobacco cultivar NCBEX1F or a tobacco hybrid derived from said tobacco cultivar NCBEX1F.

22. The tobacco product of claim 14, wherein said tobacco product is prepared from said tobacco cultivar NCBEX1MS or a tobacco hybrid derived from said tobacco cultivar NCBEX1MS.

23. The tobacco seed of claim 1, wherein said seed is from tobacco cultivar NCBEX1F or a tobacco hybrid produced from tobacco cultivar NCBEX1F.

24. The tobacco product of claim 6, wherein said tobacco product comprises tobacco material from said tobacco cultivar NCBEX1F or said tobacco hybrid produced from said tobacco cultivar NCBEX1F.

25. The tobacco product of claim 6, wherein said tobacco cultivar NCBEX1F, said tobacco cultivar essentially derived from said tobacco cultivar NCBEX1F, and said tobacco hybrid produced from said tobacco cultivar NCBEX1F comprises a percent nicotine conversion less than about 2%.

26. The tobacco seed of claim 9, wherein said seed is from tobacco cultivar NCBEX1MS or a tobacco hybrid produced from tobacco cultivar NCBEX1MS.

27. The tobacco product of claim 14, wherein said tobacco product comprises tobacco material from said tobacco cultivar NCBEX1MS or said tobacco hybrid produced from said tobacco cultivar NCBEX1MS.

28. The tobacco product of claim 14, wherein said tobacco cultivar NCBEX1MS, said tobacco cultivar essentially derived from said tobacco cultivar NCBEX1MS, and said tobacco hybrid produced from said tobacco cultivar NCBEX1MS comprises a percent nicotine conversion less than about 2%.

\* \* \* \* \*

UNITED STATES PATENT AND TRADEMARK OFFICE
CERTIFICATE OF CORRECTION

| | | |
|---|---|---|
| PATENT NO. | : 9,096,864 B2 | Page 1 of 1 |
| APPLICATION NO. | : 13/407421 | |
| DATED | : August 4, 2015 | |
| INVENTOR(S) | : Lewis et al. | |

It is certified that error appears in the above-identified patent and that said Letters Patent is hereby corrected as shown below:

In the Specification:

Column 7, Line 13: Please correct "includes an $F_t$ progeny"
to read -- includes an $F_1$ progeny --

Column 18, Line 27: Please correct "e4e5le4e5"
to read -- e4e5\e4e5 --

Signed and Sealed this
Fifteenth Day of March, 2016

Michelle K. Lee
*Director of the United States Patent and Trademark Office*